US007989219B2

(12) United States Patent
Shiotsuka et al.

(10) Patent No.: US 7,989,219 B2
(45) Date of Patent: Aug. 2, 2011

(54) BISPECIFIC CAPTURING MOLECULE

(75) Inventors: Hidenori Shiotsuka, Kawasaki (JP);
Satoru Hatakeyama, Kawasaki (JP);
Tsuyoshi Nomoto, Tokyo (JP); Masaru Kaieda, Tokyo (JP); Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 593 days.

(21) Appl. No.: 11/913,045

(22) PCT Filed: May 30, 2006

(86) PCT No.: PCT/JP2006/311180
§ 371 (c)(1),
(2), (4) Date: Oct. 29, 2007

(87) PCT Pub. No.: WO2006/129843
PCT Pub. Date: Dec. 7, 2006

(65) Prior Publication Data
US 2009/0170220 A1    Jul. 2, 2009

(30) Foreign Application Priority Data
May 31, 2005    (JP) ................................ 2005-160726

(51) Int. Cl.
*G01N 33/53*    (2006.01)
(52) U.S. Cl. ........ 436/518; 436/514; 436/810; 436/547; 435/328; 435/7.1; 435/7.94; 435/970
(58) Field of Classification Search .................. 436/514, 436/518, 810; 435/7.1, 7.94, 970
See application file for complete search history.

(56) References Cited

U.S. PATENT DOCUMENTS

| 5,529,792 | A |   | 6/1996  | Risau et al. ................. 424/570 |
|-----------|---|---|---------|---------------------------------------|
| 5,653,675 | A |   | 8/1997  | Kanno et al. ................ 588/249 |
| 5,863,789 | A |   | 1/1999  | Komatsu et al. .............. 435/262 |
| 5,910,573 | A |   | 6/1999  | Pluckthun et al. .......... 530/387.3 |
| 5,969,108 | A |   | 10/1999 | McCafferty et al. ........ 530/387.3 |
| 6,424,418 | B2 |  | 7/2002  | Kawabata et al. ............ 356/445 |
| 6,472,191 | B1 |  | 10/2002 | Yano et al. ................... 435/189 |
| 6,686,439 | B2 |  | 2/2004  | Kenmoku et al. ............ 528/272 |
| 6,803,444 | B2 |  | 10/2004 | Suzuki et al. ................ 528/361 |
| 6,825,325 | B1 | * | 11/2004 | Fischer et al. ............. 530/388.2 |
| 6,853,477 | B2 |  | 2/2005  | Nomoto et al. .............. 359/296 |
| 6,858,417 | B2 |  | 2/2005  | Yano et al. ................... 435/189 |
| 6,861,496 | B2 |  | 3/2005  | Kenmoku et al. ............ 528/272 |
| 6,864,074 | B2 |  | 3/2005  | Yano et al. ................... 435/189 |
| 6,916,861 | B2 |  | 7/2005  | Nomoto et al. .............. 523/160 |
| 6,951,745 | B2 |  | 10/2005 | Nomoto et al. .............. 435/118 |
| 7,153,622 | B2 |  | 12/2006 | Honma et al. ................ 430/105 |
| 7,235,396 | B2 |  | 6/2007  | Nomoto et al. ............ 435/253.3 |
| 2003/0194443 | A1 |   | 10/2003 | Yano et al. ................... 424/497 |
| 2004/0005638 | A1 |   | 1/2004  | Honma et al. ................ 435/7.1 |
| 2005/0208635 | A1 |   | 9/2005  | Nomoto et al. .............. 435/135 |
| 2006/0115861 | A1 |   | 6/2006  | Shiotsuka et al. ............ 435/7.9 |
| 2006/0172398 | A1 |   | 8/2006  | Nomoto et al. .............. 435/135 |
| 2006/0172399 | A1 |   | 8/2006  | Nomoto et al. .............. 435/135 |
| 2006/0275811 | A1 |   | 12/2006 | Hatakeyama et al. ........... 435/6 |
| 2007/0054315 | A1 |   | 3/2007  | Imamura et al. .............. 435/7.1 |
| 2007/0131546 | A1 |   | 6/2007  | Nomoto et al. ........... 204/403.01 |
| 2007/0131547 | A1 |   | 6/2007  | Nomoto et al. ........... 204/403.01 |
| 2007/0178522 | A1 |   | 8/2007  | Shiotsuka et al. ............ 435/7.1 |
| 2007/0190590 | A1 |   | 8/2007  | Kubo et al. ................... 435/25 |

FOREIGN PATENT DOCUMENTS

| WO | 88/06630    | 9/1988 |
| WO | 92/15606    | 9/1992 |
| WO | 93/15210    | 8/1993 |
| WO | 2004/003019 | 1/2004 |

OTHER PUBLICATIONS

Miquel A. Andrade, et al., "Comparison of ARM and HEAT Protein Repeats", J. Mol. Biol., vol. 309, 2001, pp. 1-18.
Mireille Dumoulin, et al., "A camelid antibody fragment inhibits the formation of amyloid fibrils by human lysozyme", Nature, vol. 424, Aug. 14, 2003, pp. 783-788.
Stefan Ewert, et al., "Biophysical Properties of Camelid $V_{HH}$ Domains Compared to Those of Human $V_H3$ Domains", Biochemistry, vol. 41, 2002, pp. 3628-3636.
Dario Neri, et al., "High-affinity Antigen Binding by Chelating Recombinant Antibodies (CRAbs)", J. Mol. Biol., vol. 246, 1995, pp. 367-373.
Stewart D. Nuttall, et al., "Isolation of the new antigen receptor from wobbegong sharks, and use as a scaffold for the display of protein loop libraries", Molecular Immunology, vol. 38, 2001, pp. 313-326.
Per-Åke Nygren, et al., "Binding proteins from alternative scaffolds", Journal of Immunological Methods, vol. 290, 2004, pp. 3-28.
Erin K. O'Shea, et al., "Mechanism of Specificity in the Fos-Jun Oncoprotein Heterodimer", Cell, vol. 68, Feb. 21, 1992, pp. 699-708.
Erin K. O'Shea, et al., "X-ray Structure of the GCN4 Leucine Zipper, a Two-Stranded, Parallel Coiled Coil", Science, vol. 254, No. 5031, Oct. 25, 1991, pp. 539-544.
Mehmet Sarikaya, et al., "Molecular biomimetics: nanotechnology through biology", Nature Materials, vol. 2, Sep. 2003, pp. 577-585.
Silvia Spinelli, et al., "Lateral Recognition of a Dye Hapten by a Llama VHH Domain", J. Mol. Biol., vol. 311, 2001, pp. 123-129.
Katja M. Arndt, et al., "Helix-stabilized Fv (hsFv) Antibody Fragments: Substituting the Constant Domains of a Fab Fragment for a Heterodimeric Coiled-coil Domain", Journal of Molecular Biology, vol. 312, No. 1, 2001, pp. 221-228.
Hong Seok Cheong, et al., "Affinity Enhancement of Bispecific Antibody Against Two Different Epitopes in the Same Antigen", Biochemical and Biophysical Research Communications, vol. 173, No. 3, 1990, pp. 795-800.
Katja Els Conrath, et al., "Camel Single-domain Antibodies as Modular Building Units in Bispecific and Bivalent Antibody Constructs", The Journal of Biological Chemistry, vol. 276, No. 10, Mar. 9, 2001, pp. 7346-7350.
Serge Muyldermans, "Single domain camel antibodies: current status", Molecular Biotechnology, vol. 74, 2001, pp. 277-302.

* cited by examiner

*Primary Examiner* — Bao Thuy L Nguyen
(74) *Attorney, Agent, or Firm* — Fitzpatrick, Cella, Harper & Scinto

(57) ABSTRACT

A capturing molecule having an association containing a plurality of polypeptide chains that specifically bind to different sites of a target substance, characterized in that each of the polypeptide chains has a domain having a hypervariable loop structure at a binding site binding to the target substance and an association portion for forming the association, and the polypeptide chains are associated via the association portions present in the polypeptide chains.

4 Claims, 1 Drawing Sheet

BISPECIFIC CAPTURING MOLECULE

TECHNICAL FIELD

The present invention relates to a target substance capturing molecule which is useful for isolating and detecting the target substance, a method of detecting the target substance and a kit for use in the method.

BACKGROUND ART

A biopolymer specifically binding to a target substance or a low molecular compound targeting a biomolecule is expected as a medicinal drug candidate, which binds specifically to a target substance, thereby exhibiting an effective physiological activity in a living body. Such a biopolymer or a low molecular compound is also expected as a target-substance capturing molecule of a biosensor using a specific binding ability to a target substance as described above.

As an example of such a biopolymer, an antibody may be mentioned. Antibodies bind to various foreign substances invading into the body fluid of an animal by recognizing various structures on the surfaces of the foreign substances and detoxicate these substances by its immune system. In short, antibodies are one class of the proteins functioning in a self-defense mechanism. To function such a mechanism effectively, an antibody has a molecular diversity (that is, having a number of different amino acid sequences in order to bind to various foreign substances). The number of kinds of antibodies is estimated be $10^7$ to $10^8$ per individual animal. Since an antibody has such specific antigen recognition ability, high antigen binding ability and molecular diversity, it is expected as a medicinal drug candidate and a target-substance capturing molecule.

An antibody is a protein generally having 150 kDa consisting of two of two types of polypeptide chains; one is called a heavy chain of about 50 kDa, and the other is called a light chain of about 25 kDa.

The heavy chain and the light chain each have a variable region and a constant region. The light chain is a polypeptide chain constituted of two domains; one variable region (called a light chain variable region: VL) and one constant region (CL). On the other hand, the heavy chain is a polypeptide chain constituted of 4 domains, that is, a single variable region (heavy chain variable region: VH) and three constant regions (CH1 to CH3). Each domain consists of about 110 amino acids and has a cylindrical structure, in which beta sheets are arranged in antiparallel and mutually connected via an S—S bond to form a very stable layer structure.

Antibody molecules characteristically have the binding diversification capable of binding to various types of antigens. The binding diversification is ascribed to the diversity in amino acid sequences of three complementarily determining regions (CDRs) having a loop structure and present in each of the variable regions (VH and VL).

The CDR is also called a hypervariable region. Each domain of the VH and VL has three CDRs. These CDRs are arranged on the surface of an antibody molecule and separated from each other by a region called a framework, which has a relatively common amino acid sequences between the VH and VL domains. The antibody recognizes a spatial arrangement of functional groups of a recognition site (antigenic determinant: epitope) of an object, a target substance. By virtue of this, the antibody can recognize a molecule highly specific. The presence of CDR contributes to forming a hypervariable loop structure of the antibody.

Antibodies can be produced by a method in which a desired antigenic substance is injected in combination with an adjuvant to an animal recipient (such as a rabbit, goat or mouse) at predetermined time intervals and antibodies present in the serum are recovered. Antibodies can be also produced by another method in which B cells capable of producing the antibodies are taken from the aforementioned animal recipient, fused with established tumor cells to prepare hybridoma cells, and then, the hybridoma cells are allowed to produce antibodies, followed by purifying the antibodies.

The antibodies produced by the former method contain various types of antibodies (a mixture of antibodies) recognizing different structures on the surface of the antigenic substance used in immunization. Such a serum containing a plurality of antibodies binding to a single antigen is called a polyclonal antibody. However, the antibodies produced by the latter method are called a monoclonal antibody. This is because since the antibody-producing B cells can produce only one type of antibody. The antibodies produced from one of the hybridoma cells mentioned above come to be single-type monoclonal antibodies.

In either method, an animal must be immunized by injecting a target substance, an antigen. Whether an antibody, that is, a capturing molecule capturing a desired target substance, is obtained or not cannot be confirmed until the antibodies or the serum is taken and its titer (avidity) is checked. In short, in either a polyclonal antibody or a monoclonal antibody, the characteristics of the antibody obtained vary depending upon the immune system of an animal to be immunized. Furthermore, even if the hybridoma cells capable of producing a monoclonal antibody exhibiting a binding ability to a target substance can be obtained, an efficient genetic engineering method has not yet been found for improving the binding ability of the obtained antibody, at present. Moreover, generally, production of an antibody against a target substance having an analogous structure to that of a bio-constituent of an animal recipient, such as a sugar and a lipid, cannot be expected even if it is a non-self substance. In other words, production of an antibody specifically binding to such a target substance cannot be expected in the immune system serving as a bio-defense system.

On the other hand, a combinatorial method is disclosed to obtain a capturing molecule binding to a target substance by using, for example, an antibody fragment containing at least a part of VH and VL, serving as a binding portion (such as Fab and a single chain Fv (scFv)) of an antibody to an antigen. In U.S. Pat. No. 5,969,108, there is a known technique that an antibody fragment as described above is fused with a phage, in particular, a coating protein of a fibrous phage, and used as a phage antibody having an antibody exposed on the surface. Such a phage having an antibody exposed on the surface of the coating protein is disclosed in not only U.S. Pat. No. 5,969,108 but also the pamphlet of International Publication WO 88/06630, WO 9215606, which discloses that the phage is used in a method of selecting a clone of an antibody fragment. According to these methods, a clone capable of binding a target substance can be easily obtained compared to a conventional immunization method for obtaining an antibody. In short, a conventional method for producing antibodies, which is said to be difficult to express other than in animal cells, can be improved by cleaving an antibody into fragments to lower the molecule weight.

In an antibody display method represented by the aforementioned method, first, a Lead antibody fragment binding to a target substance is obtained under a specific selection pressure and mutated by a bioengineering approach. Then, a binding/selection experiment is repeatedly performed. As a result, an antibody fragment having a higher binding ability to the target substance can be obtained. These antibody display methods have a characteristic feature in that since the complicated immune system of a living body is not used to obtain an antibody to be bound to a target substance, it does not a matter whether an antigen is self-derived or nonself-derived. Furthermore, if a gene portion encoding the CDR portion of an antibody fragment is chemically synthesized, the size of a gene library also can be enlarged.

Furthermore, U.S. Pat. No. 5,910,573 discloses a capturing molecule formed of a monomer protein with which an amphipathic helix peptide capable of forming a dimer with scFV is fused. According to the description of the invention set forth in the publication, the invention has an advantage in that amphipathic helix peptides are interacted to form a dimer, which functions as a bivalent antibody. The publication also discloses a technique regarding a bivalent specific antibody in which scFv recognizing a different antigen is fused with the helix peptide chain. However, scFv has two disulphide bonds in the polypeptide chain. The disulphide bonds are likely to serve as an obstacle to inducing folding in a correct manner when the protein is synthesized or secreted. Therefore, a problem still remains in productivity.

In J. Mol. Biol., 2001, 312, 221-228, the amphipathic helix peptide is fused with each of the heavy chain variable region (VH) and the light chain variable region (VL) constituting Fv to form a protein. According to the disclosure, unlike the case of U.S. Pat. No. 5,910,573, the polypeptide chain constituting the protein contains only a VH or VL domain. By this method, it is expected to overcome the problem of productivity as mentioned above. However, a single capturing molecule disclosed in the publication alone binds only to a single epitope. Therefore, it is difficult to impart a binding specificity superior to an antibody and antibody fragment known in the art.

J. Mol. Biol., 1995, 246, 367-373 discloses improving the binding ability of a capturing molecule to a target substance HEL. To be more specifically, the document discloses that a single chain scFv (derived from D1.3 and HyHEL10) capable of binding to HEL is genetically fused to obtain a single stranded scFv dimer, which shows improved binding ability to HEL. Similarly, International Publication WO 2004/003019 pamphlet also suggests a technology regarding a target substance-capturing molecule that recognizes two different epitopes present on the surface of the same single target substance molecule; unfortunately, it fails to mention specific techniques.

However, even in the antibody and antibody molecule obtained by such a combinatorial method and genetic engineering method, it is still difficult to obtain a clone having an excellent binding ability to a substance such as a sugar and a lipid, at present.

On the other hand, it has been suggested that the in vivo behavior of a lipid and post-translational modification of a protein have biologically significant meanings. Therefore, it is expected to apply a capturing molecule, which has a high binding ability to a substance such as a sugar and a lipid, to not only biochemical/medical fields but also wide variety of fields.

However, when a protein constituted of a recombinant single stranded scFv as mentioned above is produced in a low yield (several mg/L in *Escherichia coli*), the molecular stability of the protein tends to be low. The antibody fragments, in particular, VH and VL fragments, have a hydrophobic site at which these fragments are associated with each other. The VH and VL fragments are associated with other via the hydrophobic site to form a hetero dimer (Fv), which is stable as a molecule. However, in a folding step of a protein after protein synthesis or during the protein secretion from a cellular membrane, the hydrophobic site of the antibody fragment domain, if it is present alone, may trigger aggregation of protein or the like. In addition, it is known that the antibody fragment has a lower stability also as a molecule, compared to an antibody. This is because the antibody fragment is a recombinant protein, which is prepared by deleting a constant region thereof in order to give top priority to a binding ability to a target substance, and which has a small area between polypeptide (molecule) chains. These problems of productivity and molecular stability may be obstacles to industrial application. Technical problems still remain.

DISCLOSURE OF THE INVENTION

An object of the present invention is to provide a capturing molecule of a target substance having a desired binding ability to a target substance and ensuring stable productivity. Another object of the present invention is to provide a method of detecting a target substance by using such a capturing molecule and a kit for use in the method.

According to an aspect of the present invention, there is provided a capturing molecule comprising an association comprising a plurality of polypeptide chains that specifically bind to different sites of a target substance wherein each of the polypeptide chains has a domain having a hypervariable loop structure at a binding site binding to the target substance and an association portion for forming the association, and the polypeptide chains are associated via the association portions present in the polypeptide chains.

According to another aspect of the present invention, there is provided a capturing molecule comprising an association comprising a plurality of polypeptide chains that specifically bind to different sites of a target substance wherein each of the polypeptide chains has a domain having a binding site binding to the target substance (excluding a case having a hypervariable loop, structure at the binding site) and an association portion for forming the association, and the polypeptide chains are associated via the association portions present in the polypeptide chains.

According to the present invention, there is provided a method of detecting a target substance comprising the steps of reacting the capturing molecule having the aforementioned structure with a specimen, and detecting binding of the target substance and the capturing molecule when the specimen contains the target substance.

According to the present invention, there is provided a kit for detecting a target substance comprising the capturing molecule having the aforementioned structure, and a reagent for detecting the binding of the capturing molecule and the target substance.

In a capturing molecule according to the present invention, not less than two domains specifically recognizing different two points on the target substance are provided to the capturing molecule. These domains are defined to have a hypervariable loop structure. By the structure, a higher affinity than that of an antibody or an antibody fragment binding to a single antigen determinant (epitope) on the surface of a target substance can be imparted to the capturing molecule. Furthermore, not less than two domains specifically recognizing different two points on the target substance are provided to the capturing molecule. These domains are defined to have binding sites having a structure other than the hypervariable loop structure. By virtue of these structures, it is possible to provide a capturing molecule binding to a surface amino acid residue, which rarely binds specifically to an antibody or an antibody fragment known in the art. In short, by the combination of two types of domains, binding specificity than ever never had in the art can be imparted to the capturing molecule.

Furthermore, a capturing molecule according to the present invention is constituted of an association having a plurality of polypeptide chains associated with each other. By virtue of this, the molecular stability can be improved in the steps of manufacturing the polypeptide chains and associating them and further in various types of the solutions when the capturing molecule is applied to desired uses. Furthermore, the yields of individual polypeptide chains in a production step and a purification step can be improved. In the case of a capturing molecule having a domain of a hypervariable loop structure, molecular stability can be expected to further improve by selecting a heavy chain variable region of an antibody as the domain. Furthermore, in the case of a capturing molecule having a domain that has a binding site other than a hyper variable loop structure, the molecular recognition mechanism can be further diversified by selecting an ankyrin structure as the domain.

BEST MODE FOR CARRYING OUT THE INVENTION

Figure 1:
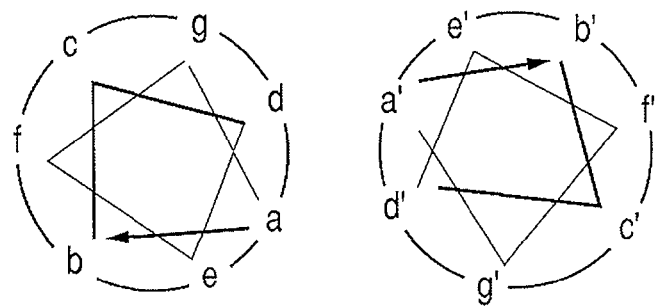
FIG. 1 is a view illustrating an alpha helical coiled coil structure.

According to a first aspect of the present invention, a target-substance capturing molecule has a domain having a hypervariable loop structure at a binding site to a target substance and constituted of an assembly of polypeptide chains, each having an association portion for forming an association, formed by associating the polypeptide chains via the association portion. In short, a plurality of domains individually have a hypervariable loop structure. The target-substance capturing molecule can be formed of, for example, a plurality of domains that have the same structure except for a variable region for recognizing a target substance.

According to a second aspect of the present invention, a target-substance capturing molecule has a domain having a structure other than a hypervariable loop structure at a binding site to a target substance and constituted of an assembly of polypeptide chains, each having an association portion for forming an association, formed by associating the polypeptide chains via the association portion. In short, a plurality of domains individually have a structure other than a hypervariable loop structure. Also in this case, the target-substance capturing molecule can be formed of, for example, a plurality of domains having the same structure except for a variable region for recognizing a target substance.

The domains formed in the capturing molecule according to these aspects have functions of recognizing different portions of a target substance to bind to them.

Now, substances to be used as a constituent ingredient of a capturing molecule according to the present invention and a method of manufacturing the same will be further explained.
(Loop Structure)

Generally, when the polypeptide chain having a plurality of loop formation sites discretely positioned thereon takes a secondary structure, they come to be sterically close to each other. The loop structure refers to such a state of a structure, by which a target site of a target substance can be specifically recognized to bind to the target site. As such a loop structure, kunitz structure may be mentioned. Such a loop structure can be formed by introducing two Cys groups at appropriate positions of a polypeptide chain.
(Hypervariable Loop Structure)

The hypervariable loop structure generally refers to the following structure. That is, when the polypeptide chain having a plurality of loop formation sites discretely positioned thereon takes a secondary structure, they come to be sterically close to each other. The hypervariable loop structure refers to such a state of the structure, by which a target site of a target substance can be specifically recognized to bind to the target site.

Examples of such a hypervariable loop structure include a hypervariable loop structure (a complex structure of 3 loops) formed of portions containing a CDR region of an antibody and fibronectin III (a complex structure of 2 to 3 loops), and further include lipocalin (a complex structure of 4 loops). The hypervariable loop structure formed of portions containing a CDR region of an antibody can be obtained from a protein classified in an immunoglobulin super family.

The domains in the VH and VL of an antibody have a common framework formed of a sandwich structure of two antiparallel beta sheets. The loop structure positioned at the end of the beta sheet sandwich structure and serves as a recognition site, CDR. There are 3 loops in each domain of an antibody. The binding ability of each antibody domain to a target substance is determined by the nature and the number of the amino acid residues forming the loop, and their sterical configuration. The variability of amino acid sequences of the loop structure contributes to the binding diversification of antibody molecules. This region is called a hypervariable loop structure of an antibody.
(Immunoglobulin Super Family)

The immunoglobulin super family refers to an antibody and protein, which are analogous to an antibody in structure and function, found in the body fluid of a living creature from fish to mammals, and produced from the lymphocytes.
(Antibody Variable Region)

An antibody is formed of 2 polypeptide chains each of which is called a heavy chain having a molecular weight of about 50 kDa and 2 polypeptide chains each of which is called a light chain having a molecular weight of about 25 kDa. The heavy chain is constituted of 4 domains: one domain (VH) called a variable region having a binding site to an antigenic substance and three domains (CH1 to CH3) called a constant region. The light chain is formed of a variable region (VL) having a binding site to an antigenic substance and a single constant region (CL). The heavy chain and the light chain are complementarily associated with each other between VH and VL and between CH1 and CL, and simultaneously, a disulphide bond is formed between CH and CL. In two heavy chains, a disulphide bond is formed at the hinge region connecting CH1 and CH2. By virtue of these bonds, the antibody can be present as a stable molecule.

In the present invention, as a domain having a binding site to a target substance, any one of the variable regions of an antibody is preferably used. As a domain having a binding site to a target substance, either VH or VL can be employed as a single domain antibody (dAb). The VH and VL serve as a binding domain at which the antibody binds to an antigen. Each of the domains VH and VL has a common framework formed of a beta sheet sandwich structure of two antiparallel beta sheets. The loop structure position at the end of the beta sandwich structure serves as a recognition site, CDR. Each domain has three loop structures. The binding ability of each domain to a target substance is determined by the characteristics, the number and configuration of amino acid residues forming the loop.

When a plurality of domains of a capturing molecule according to the present invention have a hypervariable structure, the hypervariable structure can be obtained by using at least one variable region of an antibody against an epitope of a target substance. Furthermore, the first domain may be a hypervariable structure of an antibody against an epitope of a target substance or a partial structure thereof containing at least one loop structure. Of them, the domain having a binding site to a target substance is desirable a clone of a single VH or VL having a high molecular stability. In human antibody fragments, they are classified into subfamilies based on the amino acid sequence of a relatively common region called a framework and various differences in feature between the subfamilies are disclosed by various studies so far made. In view of these findings, an assembly of a DNA library can be prepared based only on a stable framework such as VH3, which has been reported that the most stable molecular species is dominated. Subsequently, a DNA library of an antibody fragment having a stable framework of a variable region of an antibody is constructed and a gene encoding the CDR portion is chemically synthesized and introduced in the framework. Such an approach may be employed. This approach is preferable since a CDR sequence not present in the nature can be created and in view of increasing the variety of the library. Alternatively, the domain may be used by enhancing its stability by improving a factor making a molecule unstable, that is, a residue, more specifically, a hydrophobic amino acid residue present in a molecular surface such as the VH/VL interface. The aforementioned single domain structure is generally unstable in most cases, so that it may be stabilized by chemically modification with PEG. Furthermore, the dAb may be a variable region of a heavy chain of a camel antibody (VHH) (J. Mol. Biol, 311: p 123, 2001), which is present in vivo and functions as a heavy chain antibody, and a variable region IgNAR of an immunoglobulin-like molecule of nurse shark (Molecular Immunology, 2001, 38, 313-326). In particular, it is known that the variable region of a heavy chain of a camel antibody (VHH) has high molecular stability. Therefore, it may be present stably in a production/purification step and an industrially acceptable yield of VHH can be expected. The reason for such a heavy chain variable region of an antibody to exhibit molecular stability is considered as follow. As one of the reasons, mention may be made of a decreased ratio of a hydrophobic portion that is exposed in the heavy chain/light chain interface present in the variable region of an antibody formed of heavy chain/light chain. For example, a document (Biochemistry 2002, 41, 3628-3636) discloses that when the heavy chain variable region of a camel antibody is heated (80° C.) and kept cool at room temperature, the binding ability thereof can be recovered to 70 to 90%; on the other hand, when the heavy chain variable region of a human antibody is treated in the same manner, as a comparative example, it is aggregated. As described above, a heavy chain variable region in several antibodies of a camel variable region is presumed to have a very stable molecular structure. Furthermore, antibodies of camel has an advantage wherein a heavy chain fragment of a camel antibody has resides in that the length of amino acids constituting CDR3 (one of three CDRs) is long. It is known that CDR3 of a murine H chain is composed of about 9 amino acids in average and CDR3 of a human H chain is composed of about 12 amino acids; in contrast, CDR3 of a camel variable region is composed of about 18 amino acids. It has been suggested that the H-chain CDR 3 of a camel variable region becomes long in order to make up for deficiency of a light chain by increasing the number of amino acid residues, thereby compensating a decrease in degree of variety. Also, the H-chain CDR3 of a camel variable region contributes to its molecular stability by reducing the area of the hydrophobic region in contact with a solution which covers the camel antibody site corresponding to the heavy chain/light chain interface of the human or mouse antibody. Furthermore, it is suggested that the long CDR3 may bind to the valley present in an enzyme active center and bind to a low molecular compound, therefore, when an antibody fragment is singly used as a capturing molecule, variable region of camel antibody will be a useful candidate. To stabilize the structure of a heavy chain of an antibody as in the case of a camel described above, a mutation of an amino acid in connection with structural stability may be introduced into an antibody fragment of a mouse or human. Alternatively, improvement of Lead domain selected under a desired selection pressure may be performed by introducing a mutation by evolutional engineering. Such adoption of a structural feature of the heavy chain variable region of a camel antibody to a variable region of a mouse or human antibody formed of a heavy chain/light chain is possible. To describe more specifically, a mutation may be introduced into the VH/VL interface. A mutation may be introduced into any one of Val37Phe, Gly44Glu, Leu45Arg, and Trp47Gly (numerical value follows the Kabat Numbering, Sequence of Protein Immunological Interest, 5th edit, 1991).

(Domain Having a Structure of a Binding Site Other than a Hyper Variable Structure)

As a material for constituting a domain which specifically recognizes it by a structure other than a hyper variable structure and bind it, the following may be mentioned.

For example, the material may be selected from those described in the document (Journal of Immunological Method, 2004, 290, 3-28) based on the binding ability desired for a target substance. The binding ability used herein include not only the affinity for a target substance represented by an index such as $K_D$ when a complex with the target substance is formed, but also specificity sufficient to distinguish a family and a variant of a protein or a peptide when the target substance is the protein or the peptide. As a binding domain by which such a binding ability is imparted to a target-substance capturing molecule according to the present invention, a binding domain having a different molecular recognition mechanism from that of the variable region of the antibody may be mentioned. Such a recognition mechanism may be mediated via an amino acid residue on a loop formed by an intramolecular disulphide bond and an amino acid residue dotted on the discontinuous region on the surface of a secondary structure of a protein, such as an alpha helix or a beta sheet.

As the domain suitable for the present invention, it is preferable to use a molecular species having not only a binding ability to a target substance but also productivity and molecular stability. In consideration of these points, the domain (a capturing molecule) of the present invention preferably has a structure having a low molecular weight, being easily folded and being rigid after folding. Furthermore, since a scaffold portion (basal portion or sticking place) for maintaining the structure and a variable region to which a mutation is to be introduced are present, a gene encoding the variable region can be diversified. By virtue of this, it is possible to construct a protein having the structure or the library of DNA encoding the protein. Using these, a binding species to be bound to a target substance can be selected by the aforementioned combinatorial method.

Preferable examples of the binding domain satisfying the aforementioned conditions and other than those having the hypervariable loop structure include Z domain of Protein A and Z domain having a molecular recognition site formed of an alpha helix, naturally occurring ankyrin, leucine-rich repeat, armadillo structure, tetratricopeptide structure, and HEAT structure (J. Mol. Biol., 2001, 309, 1-18), and further include structural proteins having these basic structures as a motif, Zinc finger, and Knott-in structure. According to the aforementioned references, various analyses have been made on capturing molecules consisting of ankyrin and a leucine-rich repeat with respect to the structure in capturing and function. In particular, it is reported that the residue of ankyrin interacting with a target substance is primarily present in part of the externally exposed surface of a beta hairpin and the first alpha helix. It is shown that the residue interacting with a target substance can provide a large contact surface area for the interaction between the ankyrin molecule, which serves as a capturing molecule and is formed of ankyrin base structure repeats, with a target molecule. It is disclosed that, in such a binding manner, even if an amino acid residue responsible for the interaction between a capturing molecule and a target molecule and structural complementarity are not present, the surface stability can be facilitated by covering the peripheral amino acid residue of one of the capturing molecule and the target molecule by the other. According to this disclosure, a further synergetic effect may be expected. Such a binding manner cannot be observed when an antibody/antigen immune complex is formed. The binding manner is preferable since a target substance having a low binding affinity for an antibody known in the art may exhibit a higher binding affinity than that for the antibody known in the art. In a recombinant protein formed of such structure repeats, the molecular stability of the protein can be controlled by controlling the number of repeats of a unit structure. Therefore, it may be said that the recombinant protein is an excellent material from a molecular-design point of view.

Furthermore, the recombinant protein having an ankyrin structure is produced by culturing a general host cell, *Escherichia coli*, in an amount of several tens to several hundreds of mg/L. Therefore, the recombinant protein is also useful in view of productivity.

The domain having a binding site to a target substance may have a structure having the β-sheet structure analogous to that of the immunoglobulin superfamily, wherein a target substance may be recognized not by a loop structure formed between β strands but by recognizing a sugar chain molecule by a "groove" portion formed of amino acid side chains constituting the strand, for example CBM (carbohydrate-binding module) does. Furthermore, the binding domain may be a molecule selected from the Knott-in structure family, which is known to bind to a sugar and a lipid.

Furthermore, when the binding with a target substance is performed via the surface of a secondary structure in contact with a solvent, a part of the binding site may be present in the loop connecting to the secondary structure.

(The Form of a Target-Substance Capturing Molecule Capturing a Target Substance)

In a target-substance capturing molecule according to the present invention, the binding site of the capturing molecule to the target substance is formed of at least one first domain and at least one second domain. Since the binding site has not less than two binding domains different in binding manner (first domain and second domain), a single capturing molecule may have multiple types of binding functions derived from a plurality of domains.

In the present invention, the binding functions derived from a plurality of domains may be used singly or in combination of two or more, simultaneously.

When binding functions derived from a plurality of domains are used simultaneously, a capturing molecule preferably have the plurality of domains, which almost simultaneously bind to a target substance to form a complex of the target capturing molecule and the target substance. In the complex of the target capturing molecule having all domains bound to a target substance, not only $K_D$ values of individual binding sites but also the ability of forming a complex (avidity) of the capturing molecule to the target substance can be improved since $K_D$ values of individual binding sites synergistically work.

For example, in the case of a domain having a hypervariable loop structure of an antibody, when the binding ability of the domain is not sufficient even though the ability to recognize an epitope of a target substance is high, a stable binding between the domain and the target substance cannot be obtained. However, the binding ability can be improved while maintaining high recognition ability by arranging not less than two domains having a hypervariable loop structure. On the other hand, a capturing molecule having a domain, which binds a target substance via a structure other than the hypervariable loop structure, is capable of recognizing a site of a target substance, which is rarely recognized by the hypervariable loop structure. Furthermore, even in the case where a desired binding ability cannot be obtained by a single domain, a plurality of domains are arranged so that the binding ability is improved.

Moreover, the ability of the binding ability of domain mediated by a structure other than the hypervariable loop structure realizes formation of a complex with a substance which has been difficult to form a stable antigen/antibody complex with a conventional antibody/antibody fragment.

To form a complex in the state where a plurality of domains arranged in a single capturing molecule each bind to a different site of a target substance, the target substance must have a configuration which allows the domains to take sterical positions required to form such a complex.

(Association Portion of Polypeptide Chains)

A target-substance capturing molecule according to the present invention is formed as an association having a plurality of polypeptide chains associated with each other. The association is mediated via association portions present in individual polypeptide chains. The polypeptide association portion may be arranged at any position as long as it does not prevent the binding of a capturing molecule composed of them and a target substance. For example, in each binding domain, a polypeptide association site may differ from the position of binding to a target. Furthermore, in each binding domain, the binding domain binding to a target substance is discretely arranged from a polypeptide association portion as described above. At such a polypeptide association portion, association may be mediated via either a covalent bond or a non-covalent bond. The non-covalent bond used herein includes Van der Waals attraction, hydrogen bonding, ionic bonding, and hydrophobic interaction. These are due to the polypeptide association portion, in particular, an amino acid residue of the association portion.

The polypeptide association portion is preferably a peptide having a complementary interaction. Any peptide may be used as the polypeptide association portion as long as it has a complementary interaction. More specifically, the polypeptide association portion may be either an oligopeptide or a protein formed of a plurality of domains. More specifically, use may be made of an alpha domain and omega domain of beta galactosidase. Also, antibody fragments VH and VL may be used as the association portion and further alpha helical coiled coil structure, which is frequently observed in naturally occurring protein structure, may be used. The alpha helical coiled coil structure is formed of several alpha helix chains mutually interacted (associated) and wound. Two rounds of a helix are formed of 7 amino acid residues. The positions of 7 amino acid residues are usually indicated by a, b, c, d, e, f, and g as shown in FIG. 1. Hydrophobic amino acids such as Val and Ile, Glu, Lys, Gln, and Arg, which play a important role in associating helices, are used as amino acids a and d. Of them, Val and Ile are desirably used. The alpha helix coiled coil may be formed of a plurality of alpha helix chains depending upon the amino acids selected as those of the association surface. Alternatively, formation of the coiled coil structure may be induced by introducing His to the positions a and d in the co-presence of metal ions such as Co(II) and Ni(II).

As a model structure of the polypeptide association portion, mention may be made of a transcription factor GCN4 formed of a peptide having several amino acid repeats and leucine zipper such as oncogenes Fos and Jun. In the capturing molecule of the present invention, since the first binding domain and the second binding domain each bind to a different site of a target substance, alpha helical coiled-coils that are fused with the first binding domain and the second binding domain are desirably to rarely form a homodimer. In this sense, the alpha helical coiled-coils desirably form a hetero dimer such as Jun and Fos and a hetero polymer. Furthermore, it is known that a stable hetero coiled coil is formed by employing Glu in the positions e and g of the alpha helical coiled coil to be fussed with the first binding domain and Lys in the positions corresponding to these positions of the second binding domain.

Furthermore, a polypeptide association portion can be formed of polypeptide chains having oppositely charged. It is necessary for such a polypeptide association portion to have a size required so as not to prevent production of each polypeptide chains and formation of a structure required for binding of a binding domain with a target substance. More specifically, the polypeptide association portion preferably has 50 or less amino acids, and more preferably, 15 to 35 amino acids. When detection is performed by a surface plasmon resonance method, in particular, a local surface plasmon resonance method, the polypeptide association portion may be designed so as to have a length falling within the optimal range corresponding to the distribution and intensity of the spatial electric field generated in a detective element.

Forming covalent bonding at the polypeptide association portion or its peripheral portion is an efficient means in view of stabilizing a capturing molecule according to the present invention. For example, an intramolecular disulphide bond may be formed by introducing Cys into a predetermined position.

Such a bond can be formed between amino acid positions a and d, or g and e. When forming at least one of the intramolecular disulphide bonds, it is desirable that the formation of the bond does not prevent binding of the binding domain to a target substance and also does not effect on the association of the peptides. To explain more specifically, in the case of a double stranded alpha helical coiled coil, it is known that the disulphide bond formed between positions a-a is less stable in view of energy than the disulphide bond formed between positions d-d. In the case of more than three, introduction may be appropriately and selectively made. Furthermore, in accordance with the aforementioned way of thinking, a non-naturally occurring amino acid (synthetic amino acid), which is modified with an optimal linking group or has an optimal linking group introduced therein, may be introduced. In this case, a single optical functional group may not be introduced into each of all polypeptides to be associated. In other words, a single optical functional group is desirably introduced to the association portion between at least two polypeptide chains and its periphery of the association portion. When a polymer is formed of not less than three polypeptide chains, the introduction portion of an optical function group may be appropriately studied in view of the arrangement of the three polypeptide chains.

In designing, the association portion is preferably arranged so as not to prevent the binding between a binding domain and a target substance. More specifically, when the antibody fragment is used as the binding domain, in general, the polypeptide association portion is preferably fused at the C terminal of the antibody fragment and expressed as a fusion protein.

(Method for Preparing a Capturing Molecule)

A method for preparing a capturing molecule according to the present invention will be explained below. A capturing molecule according to the present invention or polypeptide chains, which are constituents of the capturing molecule, can be synthesized as follows.

A host cell for expressing a known protein is transformed with an expression vector for a desired protein designed in accordance with the host cell. The desired protein can be synthesized by use of a protein synthesis system within the host cell. Thereafter, the desired protein, which is synthesized in the host cell and secreted outside the cytoplasm, is purified from either the intracellular fraction or a cell-culture supernatant and recovered. When a secretion-type expression system is used, since a desired protein can be obtained from the culture supernatant or the periplasm, the purification step of the protein can be simplified.

In most cases, under the reducing conditions of a cell, an active-form (folded) protein is rarely obtained. However, a desired stable and active-form folded protein can be extracellularly (culture supernatant) and the periplasm. Therefore, the secretion type expression system is preferably used as a method for expressing and stably obtaining, for example, an active-form protein having an intramolecular disulphide bond. Furthermore, when an active-form recombinant protein is intracellularly expressed in a high level, the recombinant protein may be converted into insoluble granules (inclusion body) within a cell. Therefore, the expressed protein is preferably secreted outside the cell immediately upon production and kept at a concentration at which no aggregation takes place.

For example, when *Escherichia coli* is used as a host cell, a desired protein can be expressed and secreted outside the cytoplasm through the Sec system responsible for extracellular secretion by arranging a nucleic acid encoding a signal peptide known in the art and represented by pelB at the 5' side of a nucleic acid encoding the desired protein. Furthermore, it is possible to arrange a portion that encodes a plurality of polypeptide chains serving as constituents of a capturing molecule according to the present invention, in a single expression vector. In this case, by arranging the nucleic acid encoding pelB at the 5' side of each of the nucleic acids encoding individual polypeptide chains serving as constituent elements, secretion of a protein outside the cytoplasm can facilitated when the protein is expressed.

As described above, a polypeptide chain according to the present invention having a signal peptide fused to the N' terminal can be purified from a periplasm fraction and a culture supernatant fraction.

Another method is known as a method for secreting a protein in the similar manner. That is a method using not the Sac secretion system but the twin-arginine-translocation (TAT) system. This method may be useful for a protein, which is folded into an active form also in the cytoplasm. As the signal peptide, use may be made of a conventional signal peptide containing two Arg residues. Other than this, use may be made of a method using a signal peptide fused with a known protein Dsb system localized in the periplasm.

In this case, purification may be made in accordance with the following method. That is, a protein component is concentrated by ammonium sulfate or the like from the culture supernatant and the periplasm and thereafter resuspended in an appropriate buffer. Subsequently, a His-tag, which is a conventional tag for purification of a recombination protein, is inserted into the N or C terminal of a desired protein and loaded into a metal chelate column using nickel or the like. In this manner, a desired protein can be purified.

Furthermore, in the case where a desired active-form protein can be expressed in a high concentration, the desired protein may be obtained by intracellularly expressing the protein, breaking the cells and extracting the protein from a fraction having the cytoplasm dissolved therein. In the purification method, a recombination protein purification tag known in the art such as GST-tag other than the His-tag may be used. Since the GST is a highly soluble protein even by itself, it is expected that it effectively dissolves a desired protein when it is fused with GST. A polypeptide chain according to the present invention intracellularly expressed can be obtained in the form of insoluble grain. In this case, the bacterial cells obtained from a culture solution are broken by French press or ultrasonic wave, the resultant solution containing broken bacterial cells is centrifugally separated to obtain the insoluble grains. The insoluble grain fraction thus obtained is dissolved in a buffer solution containing a conventional denaturing agent such as urea and a guanidine salt and then purified by a column under denaturation conditions, in the same manner as described above. The elution fraction obtained from the column is subjected to a refolding process. In this manner, the denaturing agent can be removed and the protein can be refolded into an active form. Refolding can be performed appropriately by a method selected from methods known in the art, for example, dialysis (stepwise dialysis) and dilution known in the art in accordance with a desired protein.

In another preparation method, a desired protein may be expressed out of a living cell by using a cell extraction solution. As suitable cells used in this method, mention may be made of *Escherichia coli*, wheat germ, and rabbit reticular cells, etc.

However, protein synthesis using a cell-free extraction solution as mentioned above is generally performed under reducing conditions. Therefore, if necessary, some treatment is preferably applied to form an intramolecular disulphide bond.

In the case where a capturing molecule is formed by associating a plurality of polypeptide chains, individual polypeptide chains may be expressed either in the same host cell. Alternatively, the polypeptide chains may be expressed in different host cells and associated with each other to form a complex.

Furthermore, the present invention includes a nucleic acid encoding a polypeptide chain serving as a capturing molecule according to the present invention and a protein expression plasmid containing the nucleic acid.

(Target Substance)

The target substances serving as an object captured by a capturing molecule according to the present invention are roughly divided into non-biological substances and biological substances.

Examples of the non-biological substances that appear to be industrially variable include PCBs different in number and position of chlorine replaced and known as a pollutant; dioxins different in number and position of chlorine replaced; and endocrine disrupting chemicals called environmental hormones, such as hexachloro benzene, pentachloro phenol, 2,4,5-trichloro acetic acid, 2,4-dichlorophenoxy acetic acid, amitrole, atrazine, arachol, hexachlorocyclohexane, ethyl parathion, chlordane, oxychlordane, nonachlor, 1,2-dibromo-3-chloropropane, DDT, kelthane, aldrin, endrin, dieldrin, endosulfan (benzoepin), heptachlor, heptachlor epoxide, malathion, methomyl, methoxychlor, mirex, nitrophene, toxaphene, trifluralin, alkylphenol (having 5 to 9 carbon atoms), nonyl phenol, octyl/nonylphenol, 4-octylphenol, bisphenol A, di-2-ethylhexyl phthalate, butylbenzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitro toluene, octachlorostyrene, aldicarb, benomyl, kepone (chlorecone), mancozeb (mancozeb), maneb, metiram, metribuzin, cypermethrin, esfenvalerate, fenvalerate, permethrin, vinclozolin, zineb, ziram, dipenthyl phthalate, dihexyl phthalate, and dipropyl phthalate.

An applicable biological substance may be nucleic acids, proteins, saccharides, lipids, and complexes of these and further substances containing a biological molecule selected from the group consisting of a nucleic acid, protein, saccharide, and lipid. More specifically, the biological substance may contains a substance selected from any one of DNA, RNA, aptamer, gene, chromosome, cellar membrane, virus, antigen, antibody, lectin, hapten, hormone, receptor, enzyme, peptide, and sphingoglyco and sphingolipid. Furthermore, bacteria and cells themselves which produce the "biological substance" may be used as the "biological substance" serving as a target substance according to the present invention.

Specific examples of the protein used herein include disease markers such as alpha fetoprotein (AFP), which is an acidic glycoprotein produced in the liver cells during the fetus period and present in the fetus blood, serving as a marker of hepatic carcinoma (primary hepatic carcinoma), hepatoblastoma, metastatic hepatic carcinoma and yolk sac tumor;

PIVKA-II, which is an abnormal prothrombin emerging when the liver is substantially damaged and observed specifically in hepatic carcinoma;

BCA225, which is a glycoprotein immunohistochemically serving as a breast cancer specific antigen, serving as a marker of progressive primary breast cancer, and recurrent/metastatic breast cancer;

basic fetoprotein (BFP), which is a basic fetus protein found in the serum and an extraction solution from the intestine and blain tissue of a human fetus, serving as a marker of ovarian cancer, testicular tumor, prostatic carcinoma, pancreatic carcinoma, carcinoma of the biliary tract, hepatic carcinoma, kidney cancer, lung cancer, gastric carcinoma, bladder carcinoma, and large bowel cancer;

CA15-3, which is a sugar chain antigen, serving as a marker of progressive breast cancer, recurrent breast cancer, primary breast cancer, and ovarian cancer;

CA19-9, which is a sugar chain antigen, serving as a marker of pancreatic carcinoma, carcinoma of the biliary tract, gastric carcinoma, hepatic carcinoma, large bowel cancer, and ovarian cancer;

CA72-4, which is a sugar chain antigen, serving as a marker of ovarian cancer, breast cancer, carcinoma of the colon and rectum, gastric carcinoma, and pancreatic carcinoma;

CA125, which is a sugar chain antigen, serving as a marker of ovarian cancer (in particular, serous cystadenocarcinoma), adenocarcinoma of the uterine body, cancer of the fallopian tube, adenocarcinoma of the uterine cervix, pancreatic carcinoma, lung cancer, and large bowel cancer;

CA130, which is a glycoprotein, serving as a marker of epithelial ovarian cancer, cancer of the fallopian tube, lung cancer, hepatic carcinoma, and pancreatic carcinoma;

CA602, which is a core protein antigen, serving as a marker of ovarian cancer (in particular, serous cystadenocarcinoma), adenocarcinoma of the uterine body, and adenocarcinoma of the uterine cervix;

CA54/61(CA546), which is a sugar chain related antigen, serving as a marker of ovarian cancer (in particular, mucous cystadenocarcinoma), adenocarcinoma of the uterine cervix, and adenocarcinoma of the uterine body;

carcinoembryonic antigen (CEA), which is presently most widely used for assisting cancer diagnosis as a tumor associated marker antigen of large bowel cancer, gastric carcinoma, rectal cancer, carcinoma of the biliary tract, pancreatic carcinoma, lung cancer, breast cancer, uterine cancer, and urinary tract cancer;

DUPAN-2, which is a sugar chain antigen, serving as a marker of pancreatic carcinoma, carcinoma of the biliary tract, hepatic carcinoma, gastric carcinoma, ovarian cancer, and large bowel cancer;

elastase 1, which is present in the pancreas and a proteolytic enzyme for a protein secreted outside the pancreas specifically hydrolyzing elastic fiber, elastin of the connective tissue (constituting such as aortic wall and tendon), serving as a marker of pancreatic carcinoma, cancer of the pancreatic cysts and carcinoma of the biliary tract;

immunosuppressive acidic protein (IAP), which is a glycoprotein present in the ascites and the serum of a human cancer patient in a high concentration, serving as a marker of lung cancer, leukemia, carcinoma of esophagus, pancreatic carcinoma, ovarian cancer, kidney cancer, carcinoma of the biliary tract, gastric carcinoma, bladder cancer, large bowel cancer, thyroid cancer, and malignant lymphoma;

NCC-ST-439, which is a sugar chain antigen, serving as a marker of pancreatic carcinoma, carcinoma of the biliary tract, breast cancer, large bowel cancer, hepatic carcinoma, adenocarcinoma of lung, and gastric carcinoma;

gamma semino protein (gamma Sm), which is a glycoprotein, serving as a marker of prostatic cancer;

prostatic specific antigen (PSA), which is extracted from the prostatic tissue of a human and present only in the prostatic tissue, serving as a marker of prostatic cancer;

prostatic acidic phosphatase (PAP), which is an enzyme secreted from the prostate and hydrolyzes a phosphate ester under acidic pH, serving as a tumor marker of prostatic cancer;

nerve specific enolase (NSE), which is a glycolytic enzyme specifically present in the nerve tissue and nerve endocrine cells, serving as a marker of lung cancer (in particular, pulmonary lobule cancer), neuroblastoma, cancer of the nerve system, islet cell tumor, cancer of esophageal small cell, gastric carcinoma, kidney cancer, and breast cancer;

squamous cell carcinoma associated antigen (SCC antigen), which is a protein extracted and purified from hepatic metastatic cancer transferred from squamous cell carcinoma of the uterine cervix, serving as a marker of uterine cancer (squamous cell carcinoma of the uterine cervix), lung cancer, esophageal cancer, cancer of head and neck, and skin cancer;

serial $Le^x$-i antigen (SLX), which is a sugar chain antigen, serving as a marker of adenocarcinoma of lung, carcinoma of esophagus, gastric carcinoma, large bowel cancer, rectal cancer, pancreatic cancer, ovarian cancer, and uterus cancer;

SPan-1, which is a sugar chain antigen, serving as a marker of pancreatic carcinoma, carcinoma of the biliary tract, hepatic carcinoma, gastric cancer, and large bowel cancer;

tissue polypeptide antigen (TPA), which is a single chain polypeptide, serving as a marker of carcinoma of esophagus, gastric carcinoma, carcinoma of the colon and rectum, breast cancer, hepatic carcinoma, carcinoma of the biliary tract, pancreatic carcinoma, lung cancer, and uterine cancer, and useful in estimating a progressive cancer in combination with other tumor markers, and in recurrent prognosis/follow-up checking;

serial Tn antigen (STN), which is a core unit sugar chain antigen, serving as a marker of ovarian cancer, metastatic ovarian cancer, gastric carcinoma, large bowel cancer, carcinoma of the biliary tract, pancreatic carcinoma, and lung cancer;

CYFRA (cytokeratin), which is a tumor marker useful for detecting pulmonary lobule cancer of lung, in particular, squamous cancer of lung;

pepsinogen (PG), which is an inactive precursor of two types of pepsin (PG I·PG II), proteopepsis secreted into the gastric juice, serving as a marker of gastric ulcer (in particular, low level gastric ulcer), duodenal ulcer (in particular, recurrent and hard-to-cure), adenoma of the Brunner gland, Zollinger-Ellison Syndrome, and acute gastritis;

C-reactive protein (CRP), which is an acute phase reactive protein whose level changes in the blood plasma due to tissue damage and infection, and whose level increases when necrosis of the cardiac muscle is caused due to acute cardiac infarction;

serum amyloid A protein (SAA), which is an acute phase reactive protein and whose level changes in the blood plasma due to tissue damage and infection;

myoglobulin, which is a heme protein having a molecular weight of about 17500 and present primarily in the cardiac muscle and skeleton muscle, serving as a marker of acute cardiac infarction, muscular dystrophy, multiple myositis, and dermatomyositis;

creatine kinase (CK) (including three types of isozymes, CK-MM type derived from the skeleton muscle, CK-BB type derived from the brain and smooth muscle, and CK-MB type derived from the cardiac muscle; mitochondrial isozyme, and CK binding to immunoglobulin (macro CK)), which is an enzyme primarily present in a soluble fragment of the skeleton muscle and the cardiac muscle and released into blood by cell damage, serving as a marker of acute cardiac infarction, hypothyroidism, progressive muscular dystrophy, and multiple myositis;

troponin T, which is a protein having a molecular weight of 39,000, forming a troponin complex with troponin I and troponin C on a thin filament of the striated muscle, thereby relating to regulation of contraction of the muscle, serving as a marker of rhabdomyolysis, myocarditis, cardiac infarction, and renal failure;

ventricle myosin light chain I, which is a protein contained in both the skeleton muscle and the cardiac muscle, serving as a marker of acute cardiac infarction, muscular dystrophy, and renal failure, since an increased level of ventricle myosin light chain I means damage of the cardiac muscle and necrosis; and chromogranin A, thioredoxin, and 8-OhdG, which have been, recently attracted attention as a stress marker.

A method for detecting a target substance using a capturing molecule according to the present invention include a step of reacting the capturing molecule with a specimen and detecting binding of the target substance and the capturing molecule when the target substance is contained in the specimen.

A kit for detecting a target substance according to the present invention has a capturing molecule and a reagent for detecting the binding between the capturing molecule and the target substance. The kit for detecting a target substance may further have a reagent and a element for reacting the capturing molecule with the target substance, and a element for detecting the binding between the capturing molecule and the target substance where necessary. A detection method of the target substance and a element and a reagent for use in the method will be described below.

(Detection Kit)

A capturing molecule according to the present invention can be used for capturing a target substance and applicable to various uses employing the step of capturing a target substance. In particular, a capturing molecule according to the present invention can be preferably used in a detection method and a kit for detecting a target substance.

(Sensor Element)

As a sensor element according to the present invention, use may be made of various sensor elements known in the art.

However, sensor elements using a surface plasmon resonance method and a local surface plasmon resonance method are preferable since a label molecular such as fluorescent pigment is not required and proceeding of the binding reaction between a target substance and a capturing molecule can be monitored in real time. Particularly, detection performed by the local surface plasmon resonance method can be made by a detection element having a simple structure in which fine metal particles are fixed on the surface of a substrate. In such a sensor element, change caused by desorption and absorption of a substance taking place in the vicinity of the surface of the fine metal particles can be expressed in terms of change in dielectric constant, which is further observed in terms of change in optical characteristics (an absorption change at a predetermined wavelength or shift in an absorption-peak).

A preferable detection element for use in a local surface plasmon sensor is a target substance detection element having a substrate, a sensor element which is formed of a metal construct provided on the surface of the substrate for generating local surface plasmon resonance, and a target substance capturing body arranged on the metal construct.

(Metal Construct)

The metal construct of the present invention can be appropriately selected from those generating a local surface plasmon resonance. Examples of such a metal construct include fine metal particles arranged on a substrate and a metal thin film pattern formed on a substrate. The metal constructs are preferable since the shape of the metal construct formed on a substrate can be easily controlled and variation in measurement value by a sensor element can be minimized.

(Fine Metal Particles)

Any fine metal particles may be used as long as the particles contain a metal possibly generating a plasmon resonance phenomenon. As such a metal, gold, silver and copper are preferable. Particularly, silver is preferably used since it is excellent in sensitivity although low in corrosion resistance. Gold is also preferably used since it has advantages such that corrosion resistance is high so that a stable detection element can be manufactured, and that surface modification and immobilization with a thiol group and an amino group can be easily made. The fine metal particles can be immobilized by using a substrate whose surface is treated with an amino group or thiol group. The immobilization density may be controlled by the content of the fine metal particles in a fine metal particle solution.

(Metal Thin Film Pattern)

As a material for use in the metal thin film pattern, use may be made of a metal selected from the group consisting of gold, silver, copper and aluminium or an alloy of these. The metal thin film pattern is formed of metal dots (convex-form) aligned on a substrate or holes (concave-form) aligned in a metal thin film substrate. The shape of dots and holes may be circle, regular square, triangle, and rectangle; however may not be limited to these.

The metal pattern may be formed on a substrate via chromium or titanium thin film in view of adhesiveness to the substrate.

The metal pattern may preferably be formed with a film thickness of about 10 nm to 200 nm.

The size of the plan shape of the metal pattern, in other words, the distance from an arbitral point on the outer periphery to another point preferably fall within the range of 10 nm to 1450 nm, and further preferably, 50 nm to 450 nm. In this case, the largest distance between the arbitral two points may fall within the aforementioned range.

If necessary, not less than one metal pattern may be formed on a substrate. When a plurality of metal patterns are formed, the intervals between metal constructs preferably fall within the range of 50 nm to 2000 nm, and more preferably, 150 nm to 1000 nm. This is because the interaction due to plasmon takes place between metal constructs and influences the spatial distribution and intensity of an electric field. Furthermore, if the interval between metal constructs increases, the density of metal constructs decreases, and the intensity of a signal decreases, with the result that a special optical system must be used. Therefore, it is preferable that the interval between metal constructs falls within the aforementioned range.

A plurality of metal constructs can be formed on a substrate. More specifically, multiple types of metal constructs different in at least one of a plan shape and size may be formed on a substrate.

(Substrate)

As a material for a substrate used in the present invention may be selected from the group consisting of materials that can form a metal construct selected from the aforementioned constructs and having optical characteristics that allow detection by a plasmon resonance method. Examples of such a material include a glass substrate, quartz substrate, and plastic substrate such as polycarbonate and polyethylene terephthalate.

(Method of Producing a Sensor Element)

A method for producing a sensor element of a metal thin film pattern according to the present invention will be described. First, a metal thin film is formed on a substrate by a sputtering method or deposition method. On the thin metal film, an electron beam resist is formed by spin coating, exposed to the electron beam applied by means of an electron beam lithography apparatus, and developed to obtain a resist pattern. Thereafter, an unnecessary metal thin film is etched away. In this manner, a resist is removed to obtain a metal construct arranged in the form of desired well. Patterning can be made by an apparatus other than the electron beam lithography apparatus, such as a focused ion beam processing apparatus, X-ray exposure apparatus, and EUV exposure apparatus. Such a sensor element can be formed using a substrate having minute convexoconcave portions, which are formed by a molding method. In this case, a metal thin film is formed on a substrate by a sputtering method or a deposition method. Subsequently, the metal thin film of the substrate surface is polished to form a desired metal construct on the substrate.

(Method of Immobilizing a Capturing Molecule)

The immobilization method used herein may be selected from the group consisting of physical adsorption methods and chemical crosslinking methods known in the art. In view of using a capturing molecule on the element efficiently, it is preferable to employ an immobilization method capable of providing an orientation. An example of the immobilization method includes introduction of Cys into the C terminal of a polypeptide chain constituting a capturing molecule according to the present invention. When the surface of the sensor element is made of gold (Au), the orientation can be given by coordination of gold-thiol. When coating is applied in order to prevent non-specific adsorption of a protein onto the surface of a sensor element, processing is made such that a maleimide group can be coordinated on the surface of the coating. In this manner, a capturing molecule can be immobilized.

When a capturing molecule is immobilized by use of the Cys residue introduced into the C terminal, the capturing molecule is preferably designed to have a domain of a binding site to a target substance, and the association portion of polypeptide chains which do not have Cys residues, or to have less effect of Cys residue introduced for use in binding to the substrate produces. If such a domain or the like has Cys, a disulphide bond may be formed at an undesirable position under acidic conditions, raising problems of productivity and yield.

On the other hand, a peptide and an antibody fragment having affinity for a surface material of a substrate may be fused with the N terminal or the C terminal of a capturing molecule according to the present invention. As such a affinity peptide, use may be made of various types of peptides known in the art such as the peptides described in Nature Materials, Vol. 2, pp 577, 2003). A method of fusing a capturing molecule includes steps of inserting a nucleic acid encoding the affinity peptide into the 5' end or the 3' end of a nucleic acid encoding a peptide chain constituting a capturing molecule, and inserting the nucleic acid obtained above into an expression vector to produce a fusion protein. In a method of using an antibody fragment, an antigen against an antibody used as an immobilization tag may be immobilized onto a sensor element in advance.

The antibody fragment recognizing the surface of a sensor element may be used. More specifically, the antibody fragment is arranged at a position that will not prevent the binding between a capturing molecule and a target substance. In this manner, the capturing molecule can be immobilized onto the surface of the sensor element. As such an antibody fragment, use can be made of VH and VL of an antibody recognizing the surface of a sensor element. When the capturing molecule is constituted of a plurality of polypeptide chains associated with each other, the following method can be employed.

That is, VH having affinity for the surface of a sensor element is arranged at an end of an association portion of a polypeptide chain. To the association portion of another polypeptide chain to be associated with the aforementioned polypeptide chain, VL complementary with the VH and having affinity for the surface of the sensor element is provided directly or via a peptide linker. In this manner, a plurality of polypeptide chains are associated with each other to produce a capturing molecule and simultaneously immobilized onto the surface of the sensor element. When detection is made by a surface plasmon resonance method, in particular, a local surface plasmon resonance method, detection may preferably be performed as follows. That is, it is more desirable to design the immobilization portion of the substrate such that a capturing molecule according to the present invention can capture a target molecule within the most suitable range dealing with the spatial distribution and intensity of the electric field generating over the detection element.

On the surface of a detection element, coating can be made in the following manner in order to prevent signal generation caused by contaminants adsorbed nonspecifically. That is, the surface is coated with skim milk, casein, bovine serum albumin, phospholipid, or polyethylene glycol so as not to cover the exposed portion serving as the binding site and inhibit free movement of a capturing molecule according to the present invention.

(Detection Apparatus)

A detection apparatus for a target substance may have a structure in accordance with a detection system for the binding between a capturing molecule and the target substance. To describe more specifically, when the aforementioned detection element is formed of gold colloid, a detection apparatus may be constituted of a detection element having a metal construct and a detection means for detecting a signal from the detection element. The detection means may have an optical detection system constituted of a light source, a beam splitter and lenses, and a liquid feeding system constituted of a reaction well for performing a reaction with the detection element, and flow channel and liquid feeding mechanism for feeding a specimen (sample) to the detection element. The light source used herein preferably emits light covering the wavelength range from the visible light to infrared light. Optical determination can be made by use of an absorption spectrum, transmittance spectrum, diffusion spectrum, and reflection spectrum, and most preferably, a peak wavelength of the absorption spectrum or the intensity of the peak absorption is used. When the detection element having a metal construct specifically binds to a target substance, the peak wavelength of the adsorption spectrum shifts toward the longer wavelength side, and the absorption intensity increases. Based on degree of the shift amount and with reference to a calibration curve previously prepared by using the target substance, the amount of the target substance can be determined. Since the detection element of the present invention uses local plasmon resonance, the electric field is locally enhanced in the vicinity of the metal construct. This phenomenon can be also applied to the surface enhanced Raman spectrometry (SERS) and surface plasmon fluoro-spectrometry (SPFS). Quantitative determination of a target substance can be performed by these methods.

The reaction well and flow channel can be easily manufactured by a polydimethyl siloxane (PDMS) substrate used in an apparatus of a μTAS (micro total analysis system) type. To explain more specifically, the PDMS substrate is adhered to the substrate on which a detection element is formed to construct the structure shown in FIG. 7 for use in practice. As the liquid feeding mechanism, a micro piston pump and a syringe pump may be used.

EXAMPLES

The present invention will be more specifically explained below by way of Examples, which will not be construed as limiting the present invention.

Example 1

Preparation of Human-Lysozyme (HuL) Bound VHH-Encoding DNA Fragment

The DNA of human-lysozyme bound VHH is synthesized by an overlap PCR with reference to the sequences set forth in Nature, 2003, 424, p 783-788, PDB: 1OP9 (Sequence ID Nos. 1 and 2) of HuL bound VHH. The PCR is performed by using a pfu-turbo kit (manufactured by Stratagene) in accordance with the method recommended by the manufacturer. Restriction site NcoI is constructed at the 5' end and restriction site NotI at the 3' end. The obtained PCR fragment is designated as HuLA (Sequence ID Nos. 3 and 4).

```
                                        Sequence ID No. 2
QVQLQESGGGSVQAGGSLRLSCSASGYTYISGWFRQAPGKEREGV

AAIRSSDGTTYYADSVKGRFTISQDNAKNTVYLQMNSLKPEDTAMYYCAA

TEVAGWPLDIGIYDYWGQGTEVTVSS
                                        Sequence ID No. 4
PWQVQLQESGGGSVQAGGSLRLSCSASGYTYISGWFRQAPGKEREG

VAAIRSSDGTTYYADSVKGRFTISQDNAKNTVYLQMNSLKPEDTAMYYCAA

TEVAGWPLDIGIYDYWGQGTEVTVSSAA
```

Example 2

Preparation of Human-Lysozyme (HuL)-Bound VH-Encoding DNA Fragment

DNA encoding a VH domain shown in Sequence ID Nos. 5 and 6 is synthesized by an overlap PCR with reference to the sequence of the VH domain of Fv (PDB: 1BVK) binding to HuL at a different site from in Example 1. The PCR is performed by using a pfu-turbo kit (manufactured by Stratagene) in accordance with the method recommended by the manufacturer. The fragment is designed so as to have restriction site NcoI at the 5' end and restriction site NotI at the 3' end. The obtained PCR fragment is designated as HuLB.

```
                                        Sequence ID No. 6
QVQLQESGPGLVRPSQTLSLTCTVSGFSLTGYGVNWFRQPPGRER

EWIGMIWGDGNTDYNSALKSRVTMLKDTSKNQFSLRLSSVTAADTAVYYC

ARERDYRLDYWGQGSLVTVSSG
```

Example 3

Preparation of an Expression Plasmid of HuL-Bound VH-Protein HulA/HulB

Using the PCR fragments HulA/HulB obtained in Example 1 and Example 2, an expression plasmid of HuL-bound VH-protein is separately prepared. The vector used herein is pET-24d (manufactured by Novagen).

(1) HuLA obtained in Example 1, HuLB obtained in Example 2, and pET-24d are separately digested by restriction enzymes NcoI and NotI (both are manufactured by New England Biolabs) in accordance with the method recommended by the manufacturer and described in the technical bulletin.

(2) The resultant solutions containing enzyme reaction products are separately subjected to agarose gel electrophoresis.

(3) An about 0.4 kbp fragment is cleaved out from a reaction product in a HuL-B reaction solution and a 5.3 kbp fragment from a pET-24d reaction solution and separately purified by a purification kit (manufactured by Promega, trade name: Wizard SV Gel and PCR Clean-Up System).

(4) The DNA fragments (a combination of HuLA fragment and pET-24d and a combination of HuLB and pET-24d) obtained above are ligated with T4-Ligase (manufactured by Roche) for 2 hours in accordance with the method recommended by the manufacturer.

(5) JM109 competent cells (manufactured by Promega) are transformed by use of the resultant ligation solution in accordance with a heat shock method (placed in ice, transferred to 42° C. for 90 sec, and transferred again into ice). After the heat shock treatment, 750 μL of LB medium (10 g of tryptone, 5 g of yeast extract, and 10 g sodium chloride/L) is added to the resultant solution and cultured at 37° C. for 1 hour while shaking. The obtained solution is centrifuged at 6000 rpm for 5 minutes and 700 μL of the supernatant is discarded.

(6) The remaining culture solution and the precipitate are stirred, spread on an LB/ampicillin (100 μg/mL) agar plate, and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the plasmid thus obtained is analyzed and checked whether a desired DNA fragment is inserted or not. The plasmids obtained herein are designated as pET-HuLA and pET-HuLB.

Example 4

Expression of a HuL Bound VH Protein HuLA/HuLB (1) Transformation

BL21(DE3) is transformed with the pET-HuLA and pET-HuLB obtained in Example 3 by the heat shock transformation method employed in Example 3, similarly, spread on a LB/ampicillin agar plate, and allowed to stand still at 28° C. for 16 hours. HuLA and HuLB are separately subjected to the following operation.

(2) Preliminary Culture

A colony is arbitrarily selected from those grown on the plate is arbitrarily selected and cultured in 3.0 mL LB/ampicillin medium at 28° C. overnight while shaking.

(3) Full-Scale Culture

The preliminary culture solution is poured in 750 mL of 2×YT medium and continued to culture at 28° C. At the time point when OD600 exceeds 0.8, IPTG is added up to a final concentration of 1 mM and continuously cultured at 28° C. overnight.

(4) Purification (4-1) Acquisition of Cytoplasm Fraction

The culture solution is centrifuged at 6000 rpm for 30 minutes at 4° C. and the culture supernatant is discarded to obtain a bacterial fraction. To the bacterial fraction thus obtained, 15 mL of 20 mM Tris/500 mM NaCl (pH 7.9) (hereinafter referred to as "Tris solution") is added and resuspended well. The bacterial cells are broken by a French press to obtain a cytoplasm fraction as a solution containing broken cells.

(4-2) Metal Chelate Column

A desired protein is purified from the cytoplasm fraction by use of a His tag fused with the C terminal of the desired protein.

As a metal chelate column carrier, His-Bind (manufactured by Novagen) is used. Steps for preparing a column, loading a sample, and washing are performed at 4° C. in accordance with the method recommended by the manufacturer. The desired protein, that is, His-tag fusion protein, is eluted by a 500 mM imidazole/Tris solution.

(4-3) Gel Chromatography

Purification is performed by gel filtration using Sephadex 75 (manufactured by Amersham Bioscience) in a buffer containing 50 mM Tris-HCl, 200 mM NaCl, 1 mM EDTA, pH 8, at a flow rate of 0.7 mL/min at 4° C. The peak suggesting that HuLA and HuLB both are a protein monomer of about 1.3 kDa, is taken and subjected to the following evaluation analyses.

The eluate solution is dialyzed against a Tris solution used as an external solution to remove imidazole from the eluate solution. Subsequently, the external solution is replaced by a phosphate buffer (hereinafter referred to as PBS). In this way, buffer replacement is performed to obtain a solution for SPR evaluation.

Example 5

Evaluation of SPR

As a substrate, CM5 (manufactured by BIAcore) is used. HuL is immobilized onto the substrate in accordance with the method recommended by the manufacturer. The HuL immobilized chip thus obtained is subjected as an immobilization chip to evaluation under the conditions: running buffer: 0.1% Tween 20/PBS, flow rate: 20 µL/min, and temperature: 25° C. As a result evaluated by SPR, a dissociation constant for HuLA and HulB shows $10^{-7}$ M and $10^{-6}$ M respectively. It is demonstrated that both bind to the HuL immobilized.

Example 6

Preparation of Human-Lysozyme (HuL) Bound VHH-Encoding DNA Fragment

The DNA of HuL bound VHH is synthesized by an overlap PCR with reference to the sequences set forth in Nature, 2003, 424, p 783-788, PDB: 1OP9 (Sequence ID Nos. 1 and 2) of MBP bound VHH. The PCR is performed by using a pfu-turbo kit (manufactured by Stratagene) in accordance with the method recommended by the manufacturer. Restriction site NcoI is constructed at the 5' end and restriction site EcoRI at the 3' end. The obtained PCR fragment is designated as HuLA2 (Sequence ID Nos. 7 and 8).

Sequence ID No. 8
PWQVQLQESGGGSVQAGGSLRLSCSASGYTYISGWFRQAPGKERE

GVAAIRSSDGTTYYADSVKGRFTISQDNAKNTVYLQMNSLKPEDTAMYYC

AATEVAGWPLDIGIYDYWGQGTEVTVSSEF

Example 7

Preparation of Human-Lysozyme (HuL)-Bound VH-Encoding DNA Fragment

DNA encoding a VH domain shown in Sequence ID Nos. 9 and 10 is synthesized by an overlap PCR with reference to the sequence of the VH domain of Fv (PDB: 1BVK) binding to HuL at a different site from in Example 1. The PCR is performed by using a pfu-turbo kit (manufactured by Stratagene) in accordance with the method recommended by the manufacturer. The fragment is designed so as to have restriction site NcoI at the 5' end and restriction site EcoRI at the 3' end. The obtained PCR fragment is designated as HuLB2.

Sequence ID No. 10
PWQVQLQESGPGLVRPSQTLSLTCTVSGFSLTGYGVNWFRQPPGR

EREWIGMIWGDGNTDYNSALKSRVTMLKDTSKNQFSLRLSSVTAADTAVY

YCARERDYRLDYWGQGSLVTVSSGEF

Example 8

Preparation of an Expression Plasmid of HuL-Bound VH-Protein HulA/HulB

Using the PCR fragments HulA2 and HulB2 obtained in Example 1 and Example 2, expression plasmids of HuL-bound VH-protein are separately prepared. The vector used herein is pET-24d (manufactured by Novagen).

(1) HuLA obtained in Example 1, HuLB obtained in Example 2, and pET-24d are digested by restriction enzymes NcoI and EcoRI (both are manufactured by New England Biolabs) in the method recommended by the manufacturer and described in the technical bulletin.

(2) The resultant solutions containing enzyme reaction products are separately subjected to agarose gel electrophoresis.

(3) An about 0.4 kbp fragment is cleaved out from a reaction product in a HuL-B reaction solution and a 5.3 kbp fragment from a pET-24d reaction solution and separately purified by a purification kit (manufactured by Promega, trade name: Wizard SV Gel and PCR Clean-Up System).

(4) The DNA fragments (a combination of HuLA fragment and pET-24d and a combination of HuLB and pET-24d) obtained above are ligated with T4-Ligase (manufactured by Roche) for 2 hours in accordance with the method recommended by the manufacturer.

(5) JM109 competent cells (manufactured by Promega) are transformed by use of the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant solution and cultured at 37° C. for 1 hour while shaking. The obtained solution is centrifuged at 6000 rpm for 5 minutes and 700 µL of the supernatant is discarded.

(6) The remaining culture solution and the precipitate are stirred, spread on an LB/ampicillin (100 µg/mL) agar plate, and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the plasmid thus obtained is analyzed and checked whether a desired DNA fragment is inserted or not. The plasmids obtained herein are designated as pET-HuLA2 and pET-HuLB2.

Example 9

Preparation of Alpha Helical Coiled Coil DNA Fragment

DNA encoding a Jun protein Zipper sequence is synthesized by an overlap PCR with reference to the sequence thereof shown in Science, 1992, 254, 539-544. PCR is performed by using a pfu-turbo kit (manufactured by Stratagene) in accordance with the method recommended by the manufacturer. Restriction site EcoRI is inserted to the 5' end and HindIII at the 3' end of the synthetic DNA (Sequence ID Nos. 11 and 12) thus prepared. In the same manner, DNA encoding Fos protein shown in Cell, 1992, 68, 699-708 is synthesized. Restriction site EcoRI is inserted to the 5' end and HindIII to the 3' end of the synthetic DNA (Sequence ID Nos. 13 and 14) thus prepared. The synthetic DNA fragments obtained above are designated as G3jun and G3fos, respectively.

Sequence ID No. 12
EFGGGGSGGGGSGGGGSRIARLEEKVKTLKAQNSELASTANMLRE

QVAQLKQKVMNYRLC

Sequence ID No. 14
EFGGGGSGGGGSGGGGSLTDTLQAETDQLEDKKSALQTEIANLLK

EKEKLEFILAAYRLC

Example 10

Preparation of a Plasmid Expressing HuLA-Jun Fusion Protein

To pET-HuLA2 obtained in Example 8, the PCR fragment G3jun obtained in Example 9 is inserted to prepare a plasmid expressing HuLA-Jun fusion protein.

(1) The pET-HuLA2 obtained in Example 8, and the synthetic DNA G3jun obtained in Example 9 are cleaved by restriction enzymes EcoRI and HindIII (both are manufactured by New England Biolabs) in the method recommended by the manufacturer and described in the technical bulletin.

(2) The resultant solutions containing enzyme reaction products are subjected to agarose gel electrophoresis.

(3) An about 0.5 kbp fragment is cleaved out from a reaction product in a G3-jun reaction solution and a 5.7 kbp fragment from a pET-HuLA2 reaction solution and purified by a purification kit (manufactured by Promega, trade name: Wizard SV Gel and PCR Clean-Up System).

(4) The DNA fragments obtained above are ligated with T4-Ligase (manufactured by Roche) for 2 hours in accordance with the method recommended by the manufacturer.

(5) JM109 competent cells (manufactured by Promega) are transformed by the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant solution and cultured at 37° C. for 1 hour while shaking. The obtained solution is centrifuged at 6000 rpm for 5 minutes and 700 µL of the supernatant is discarded.

(6) The remaining culture solution and the precipitate are stirred and spread on an LB/ampicillin (100 µg/mL) agar plate and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the obtained plasmid is analyzed and checked whether a desired DNA fragment (Sequence ID Nos. 15 and 16) is inserted or not. The plasmid obtained herein is designated as pET-VA2J.

Sequence ID No. 16
QVQLQESGPGLVRPSQTLSLTCTVSGFSLTGYGVNWFRQPPGREREWIGM

IWGDGNTDYNSALKSRVTMLKDTSNNQFSLRLSSVTAADTAVYYCARERD

YRXDYWGQGSLVTVSSGESGGGGSGGGGSGGGGSRIARLEEKVKTLKAQN

SELASTANMLREQVAQLKQKVMNYRLC

Example 11

Preparation of a Plasmid Expressing Both HuLA-Jun Fusion Protein and HuLB-Fos Fusion Protein A plasmid expressing HuLB-Fos fusion protein is prepared by using the PCR fragments obtained in Examples 7 and 9. The vector used herein is pET-24d (manufactured by Novagen).

(1) Synthetic DNA HuLB2 obtained in Example 7 and pET-24d are cleaved by restriction enzymes NcoI and EcoRI (both are manufactured by New England Biolabs) in the method recommended by the manufacturer and described in the technical bulletin.

(2) The resultant solutions containing enzyme reaction products are subjected to agarose gel electrophoresis.

(3) An about 0.4 kbp fragment is cleaved out from a reaction product in a HuLB2 reaction solution and a 5.3 kbp fragment from a pET-24d reaction solution and purified by a purification kit (manufactured by Promega, trade name: Wizard SV Gel and PCR Clean-Up System).

(4) The DNA fragments obtained above are ligated with T4-Ligase (manufactured by Roche) for 2 hours in accordance with the method recommended by the manufacturer.

(5) JM109 competent cells (manufactured by Promega) are transformed by use of the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant solution and cultured at 37° C. for 1 hour while shaking. The obtained solution is centrifuged at 6000 rpm for 5 minutes and 700 µL of the supernatant is discarded.

(6) The remaining culture solution and the precipitate are stirred and spread on an LB/ampicillin (100 µg/mL) agar plate and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the plasmid thus obtained is analyzed and checked whether a desired DNA fragment is inserted or not. The plasmid obtained herein is designated as pET-HuLB2.

(10) The obtained pET-HuLB2 and synthetic DNA fragment G3fos obtained in Example 9 are digested with restriction enzymes EcoRI and HindIII (both manufactured by NEB) in accordance with the method recommended by the manufacturer.

(11) The solutions containing reaction products with enzymes are subjected to agarose gel electrophoresis.

(12) An about 0.5 kbp fragment is cleaved out from a reaction product in a G3-fos solution and a 5.7 kbp fragment from a pET-HuLB2 solution and purified by a purification kit (manufactured by Promega, trade name: Wizard SV Gel and PCR Clean-Up System). Subsequently, the aforementioned steps (4) to (8) are repeated.

(13) The sequence of the plasmid thus obtained is analyzed to confirm whether a desired DNA fragment (Sequence ID Nos. 17 and 18) is inserted or not. The plasmid obtained herein is designated as pET-VB2F.

Sequence ID No. 18

QVQLQESGPGLVRPSQTLSLTCTVSGFSLTGYGVNWFRQPPGREREWIGM

IWGDGNTDYNSALKSRVTMLKDTSNNQFSLRLSSVTAADTAVYYCARERD

YRXDYWGQGSLVTVSSGESGGGGSGGGGSGGGGSLTDTLQAETDQLEDKK

SALQTEIANLLKEKEKLEFILAAYRLC

(14) PCR is performed using pET-AF as a template and primers BF-fw and AF-Bk by a pfu-turbo kit (manufactured by Stratagene) in accordance with the method recommended by the manufacturer to obtain an about 0.7 kbp fragment dna_vb2f.

(15) The pET-VB2J obtained in Example 10 and synthetic DNA, dna_vb2f, obtained in the step (14) are cleaved by restriction enzymes SphI and BghI (both are manufactured by New England Biolabs) in accordance with the method recommended by the manufacturer.

(16) The resultant enzyme reaction solutions are subjected to agarose gel electrophoresis.

(17) An about 0.7 kbp fragment is cleaved out from a reaction product in a dna_vb2f reaction solution and a 6.1 kbp fragment from a pET-VA2J reaction product and purified by a purification kit (manufactured by Promega, trade name: Wizard SV Gel and PCR Clean-Up System). Subsequently, the aforementioned steps (4) to (8) are repeated.

(18) The sequence of the plasmid thus obtained is analyzed to confirm whether a desired DNA fragment is inserted or not. The plasmid simultaneously expressing both human lysozyme-bound HuLA-JUN fusion protein and human lysozyme-bound HuLB-Fos fusion protein is designated as pET-VA2FVB2J.

Example 12

Expression of a Plasmid Expressing Both HuLA-Jun Fusion Protein and HuLB-Fos Fusion Protein (1) Transformation BL21(DE3) is transformed with the pET-VA2FVB2J obtained in Example 11 by the heat shock transformation method used in Example 3, similarly spread on a LB/ampicillin agar plate, and allowed to stand still at 28° C. for 16 hours.

(2) Preliminary Culture

A colony is arbitrarily selected from those grown on the plate and cultured in 3.0 mL LB/ampicillin medium at 28° C. overnight while shaking.

(3) Full-Scale Culture

The preliminary culture solution is poured in 750 mL of 2×YT medium and continued to culture at 28° C. At the time point when OD600 exceeds 0.8, IPTG is added up to a final concentration of 1 mM and culturing is continuously performed at 28° C. overnight.

(4) Purification (4-1) Acquisition of Cytoplasm Fraction

The culture solution is centrifuged at 6000 rpm for 30 minutes at 4° C. and the culture supernatant is discarded to obtain a bacterial fraction. To the bacterial fraction, 15 mL of Tris solution is added and sufficiently resuspended. The bacterial cells are broken by a French press to obtain a cytoplasm fraction as a solution containing broken cells.

(4-2) Metal Chelate Column

A desired protein is purified from the cytoplasm fraction by use of a His tag fused with the C terminal of the desired protein.

As a metal chelate column carrier, His-Bind (manufactured by Novagen) is used. Steps for preparing a column, loading a sample, and washing are performed at 4° C. in accordance with the method recommended by the manufacturer. The desired protein, that is, His-tag fusion protein, is eluted by a 500 mM imidazole/Tris solution.

(4-3) Gel Chromatography

Purification is performed by gel filtration using Sephadex 75 (manufactured by Amersham Bioscience) in a buffer containing 50 mM Tris-HCl, 200 mM NaCl, 1 mM EDTA, pH 8, at a flow rate of 0.7 mL/min at 4° C. The peak suggesting a protein monomer of about 20 kDa is taken and subjected to the following evaluation analyses. The eluate solution is again dialyzed against a Tris solution used as an external solution to remove imidazole in the eluate solution. Subsequently, the external solution is replaced by PBS. In this way, buffer replacement is performed to obtain a solution for SPR evaluation.

Example 13

The human lysozyme-bound HuLA-Jun/human lysozyme-bound HuLB-Fos hetero dimer obtained in Example 12 was evaluated by SPR (manufactured by BIAcore) in the same manner as in Example 5. As a substrate, CM5 is used. Human lysozyme is immobilized onto the substrate in accordance with the method recommended by the manufacturer and used as a human lysozyme immobilization chip in the evaluation under the conditions: running buffer: 0.1% Tween 20/PBS, flow rate: 20 μL/min, and temperature: 25° C. As a result evaluated by SPR, dissociation constant for the hetero dimer shows $10^{-9}$M. The capturing molecule according to the present invention has a high binding ability compared to the capturing molecule known in the art binding to a target substance at a single epitope (or single site).

Example 14

Preparation of LSPR Sensor Element (1)

A sensor element is prepared by adding 200 μl of a gold colloidal solution (100 nmφ manufactured by Tanaka Kikinzoku) to the wells of an amino-treated titer plate (manufactured by Sumitomo Bakelite Co., Ltd.) and allowed to stand still at room temperature for 24 hours. Subsequently, the gold colloidal solution is removed from each of the wells, 200 µl of pure water is added and shaken for 10 minutes to remove the pure water added. This operation is repeatedly performed three times. Thereafter, the wells are dried by nitrogen gas. In this manner, it is confirmed that 20 to 25% of the bottom area of each well is covered by fine golden particles.

The absorption spectrum obtained after 200 µl of the PBS solution is added to the wells of the sensor element of this Example has a peak at wavelength of near 510 nm.

Example 15

Preparation of LSPR Detection Element (1)

To impart a target substance capturing ability to the sensor element prepared in Example 14, the protein obtained in Example 12 is used as a target substance capturing material. A method of immobilizing the protein onto the surface of a golden construct will be explained below. First, 0.05% Tween 20/PBS solution is prepared so as to contain the protein obtained in Example 12 having a thiol group (having a high affinity for gold, a material for the construct of this Example) at the carboxyl terminal in an amount of 1 µM.

The protein solution thus obtained is dispensed to the wells of the detection element obtained in Example 14 in an amount of 200 µl per well. After the wells are allowed to stand still at room temperature for 2 hours, the solution is removed from the wells. Subsequently, 200 µL of the 0.05% Tween 20/PBS solution is added to each well. After the wells are shaken for 10 minutes, the 0.05% Tween20/PBS solution added above is removed. This operation is repeatedly performed three times. By virtue of this operation, the peak of the absorption spectrum obtained after 200 µl of the PBS solution is added to the wells of the sensor element, shifts toward a wavelength of near 530 nm.

The concentration of human lysozyme in a specimen can be specifically determined by use of the detection element obtained in this Example in accordance with the following operation. To each of the wells of the detection element of this Example, a specimen containing a target substance, human lysozyme, is added and allowed to stand still for 2 hours. In this way, human lysozyme is captured by the wells. After the specimen is removed from each of the wells, 200 µL of a 0.05% Tween 20/PBS solution is added to each well and shaken for 5 minutes and then the 0.05% Tween 20/PBS solution added above is removed. This operation is repeatedly performed three times. Furthermore, the same operation is repeated three times by replacing the solution with a PBS solution to wash the wells.

Finally, a PBS solution is added to the wells and the absorption spectrum is obtained.

By comparing absorption spectra before and after the reaction, it is observed that the peak shifts when a target substance is bound to the surface of the detection element by a specific antigen-antibody reaction. The intensity of the peak of the absorption spectrum or the correlation between the shift amount of the peak wavelength and the human-lysozyme concentration has been obtained by use of a human lysozyme control solution of which concentration is known. Therefore, the human lysozyme concentration of the specimen can be obtained.

Example 16

Preparation of LSPR Sensor Element (2)

Figure 2:
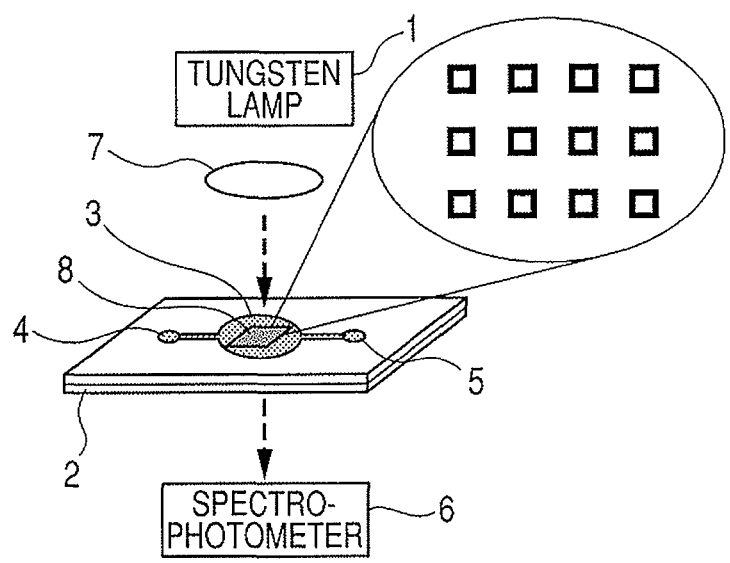
FIG. 2 is a schematic view of a detection apparatus used in Examples 17 and 18.
Figure 3:
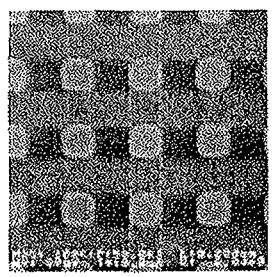
FIG. 3 is a SEM photograph of a sensor element according to Example 17.

FIG. 2 shows a schematic structure of the detection apparatus used in this Example. A detection element 8 was prepared by forming a thin golden film of 20 nm thick on a quartz substrate of 625 µm thick and patterning the film into a predetermined pattern by an electron beam lithography apparatus. Light from tungsten lamp 1 is collimated by a collimator lense 7. Absorption spectrum of transmitted light through element 8 is obtained by spectro-photometer 6. Reference numeral numbers 2, 3, 4 and 5 indicate substrate, reaction well, inlet and outlet respectively. As shown in the SEM (scanning electron microscopic) photograph of FIG. 3, the outer shape of the planar metal construct is a regular square of 200 nm×200 nm. The shape of the internal opening portion is not always formed in the same as that of the outer shape depending upon the resolution (high or low resolution). In the pattern, metal constructs are arranged in the form of array at the intervals of 250 nm in the area of 3 mm×3 mm. The absorption spectrum of the construct has a peak a wavelength of near 800 nm.

Example 17

Preparation of LSPR Detection Element (2)

Next, the capturing molecule of Example 12 is immobilized onto the surface of the metal construct of Example 16. A method for immobilizing the capturing molecule onto the surface of a golden construct surface will be described below.

First, 0.05% Tween 20/PBS solution is prepared so as to contain the protein obtained in Example 12 having a thiol group (having a high affinity for gold, which is a material for the construct of Example 16) at the carboxyl terminal in an amount of 1 µM. The protein solution thus obtained is dispensed to the arrays of the detection element obtained in Example 16 in an amount of 200 µl per array. After the array is allowed to stand still at room temperature for 2 hours, the solution is removed from the array. Subsequently, 200 µL of the 0.05% Tween 20/PBS solution is added to each array. After the array is shaken for 10 minutes, the 0.05% Tween 20/PBS solution added above is removed. This operation is repeatedly performed three times. By virtue of this operation, the surface of the construct is modified by the capturing molecule of Example 12.

Example 18

Evaluation of LSPR (2)

The concentration of human lysozyme contained in a specimen can be specifically determined by the operation below.

(1) A specimen containing a target substance, human lysozyme, is fed into the element manufactured above through an inlet 4 and human lysozyme is captured by the construct.

(2) The specimen is discharged and a phosphate buffer is fed through the inlet 4 to wash the interior of a reaction well 3.

(3) Finally, the phosphate buffer is loaded and the absorption spectrum of the golden construct is obtained.

The absorption spectra are compared before and after the reaction. When a target substance is bound to the surface of the detection element by a specific antigen-antibody reaction, the peak of the absorption spectrum shifts.

The intensity of the peak of the absorption spectrum or the correlation between the shift amount of the peak wavelength and the human lysozyme concentration has been obtained by use of a human lysozyme control solution known in concentration. Therefore, even a very low human lysozyme concentration can be obtained in a specimen of an unknown concentration.

This application claims priority from Japanese Patent Application No. 2005-160726 filed May 31, 2005, which is hereby incorporated by reference herein.

The invention claimed is:

1. A capturing molecule comprising an association comprising a plurality of polypeptide chains that specifically bind to different sites of a target substance,
   wherein each of the polypeptide chains has a domain having a hypervariable loop structure at a binding site binding to the target substance and an association portion for forming the association,
   wherein the domain is a heavy chain variable region of a camel antibody,
   wherein the polypeptide chains are associated via the association portions present in the polypeptide chains, and
   wherein the association portions are formed of a peptide having several amino acid repeats and a leucine zipper.

2. A method of detecting a target substance comprising the steps of
   reacting the capturing molecule according to claim 1 with a specimen, and
   detecting binding of the target substance and the capturing molecule when the specimen contains the target substance.

3. An apparatus for detecting a target substance comprising the capturing molecule according to claim 1,
   a detecting element having the capturing molecule provided on at least one portion of a surface thereof,
   holding means for holding the element, and
   detecting means for detecting the target substance by the element.

4. A kit for detecting a target substance comprising the capturing molecule according to claim 1, and
   a reagent for detecting binding of the capturing molecule and the target substance.

* * * * *

SEQUENCE LISTING

```
<160> NUMBER OF SEQ ID NOS: 18

<210> SEQ ID NO 1
<211> LENGTH: 363
<212> TYPE: DNA
<213> ORGANISM: Artificial
<220> FEATURE:
<223> OTHER INFORMATION: Human Lysozyme -binding ValHH coding DNA

<400> SEQUENCE: 1
caggtgcagc tgcaggaaag cggcggtggc agcgtgcagg cgggcggtag cctgcgcctg      60
agctgcagcg cgagcggcta tacctatatt agcggctggt ttcgccaggc gccgggcaaa     120
gaacgcgaag gcgtggcggc gattcgcagc agcgatggca ccacctatta tgcggatagc     180
gtgaaaggcc gctttaccat tagccaggat aatgcgaaaa ataccgtgta tctgcagatg     240
aatagcctga aaccggaaga taccgcgatg tattattgag cggcgaccga agtggcgggc     300
tggccgctgg atattggcat ttatgattat tggggccagg gcaccgaagt gaccgtgagc     360
agc                                                                    363

<210> SEQ ID NO 2
<211> LENGTH: 121
<212> TYPE: PRT
<213> ORGANISM: Artificial
<220> FEATURE:
<223> OTHER INFORMATION: Human Lysozyme -binding VHH

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Ser Ala Ser Gly Tyr Thr Tyr Ile Ser Gly
            20                  25                  30

Trp Phe Arg Gln Ala Pro Gly Lys Glu Arg Glu Gly Val Ala Ala Ile
        35                  40                  45

Arg Ser Ser Asp Gly Thr Thr Tyr Tyr Ala Asp Ser Val Lys Gly Arg
    50                  55                  60

Phe Thr Ile Ser Gln Asp Asn Ala Lys Asn Thr Val Tyr Leu Gln Met
65                  70                  75                  80

Asn Ser Leu Lys Pro Glu Asp Thr Ala Met Tyr Tyr Cys Ala Ala Thr
                85                  90                  95

Glu Val Ala Gly Trp Pro Leu Asp Ile Gly Ile Tyr Asp Tyr Trp Gly
            100                 105                 110

Gln Gly Thr Glu Val Thr Val Ser Ser
        115                 120

<210> SEQ ID NO 3
<211> LENGTH: 377
<212> TYPE: DNA
<213> ORGANISM: Artificial
<220> FEATURE:
<223> OTHER INFORMATION: Human Lysozyme -binding VHH coding DNA

<400> SEQUENCE: 3
ccatggcagg tgcagctgca ggaaagcggc ggtggcagcg tgcaggcggg cggtagcctg      60
cgcctgagct gcagcgcgag cggctatacc tatattagcg gctggtttcg ccaggcgccg     120
```

```
ggcaaagaac gcgaaggcgt ggcggcgatt cgcagcagcg atggcaccac ctattatgcg    180
gatagcgtga aaggccgctt taccattagc caggataatg cgaaaaatac cgtgtatctg    240
cagatgaata gcctgaaacc ggaagatacc gcgatgtatt attgagcggc gaccgaagtg    300
gcgggctggc cgctggatat tggcatttat gattattggg ccagggcac cgaagtgacc     360 gtgagcagcg cggccgc                                                   377
```

<210> SEQ ID NO 4
<211> LENGTH: 125
<212> TYPE: PRT
<213> ORGANISM: Artificial
<220> FEATURE:
<223> OTHER INFORMATION: Human Lysozyme -binding VHH

<400> SEQUENCE: 4

```
Pro Trp Gln Val Gln Leu Gln Glu Ser Gly Gly Gly Ser Val Gln Ala
1               5                   10                  15

Gly Gly Ser Leu Arg Leu Ser Cys Ser Ala Ser Gly Tyr Thr Tyr Ile
            20                  25                  30

Ser Gly Trp Phe Arg Gln Ala Pro Gly Lys Glu Arg Glu Gly Val Ala
        35                  40                  45

Ala Ile Arg Ser Ser Asp Gly Thr Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Ala
                85                  90                  95

Ala Thr Glu Val Ala Gly Trp Pro Leu Asp Ile Gly Ile Tyr Asp Tyr
            100                 105                 110

Trp Gly Gln Gly Thr Glu Val Thr Val Ser Ser Ala Ala
        115                 120                 125
```

<210> SEQ ID NO 5
<211> LENGTH: 351
<212> TYPE: DNA
<213> ORGANISM: Artificial
<220> FEATURE:
<223> OTHER INFORMATION: Human Lysozyme -binding mutated VH coding DNA

<400> SEQUENCE: 5

```
caggtgcagc tgcaggaaag cggcccgggc ctggtgcgcc cgagccagac cctgagcctg    60
acctgcaccg tgagcggctt tagcctgacc ggctatggcg tgaattggtt tcgccagccg    120
ccgggccgcg aacgcgaatg gattggcatg atttggggcg atggcaatac cgattataat    180
agcgcgctga aaagccgcgt gaccatgctg aaagatacca gcaataatca gtttagcctg    240
cgcctgagca gcgtgaccgc ggcggatacc gcggtgtatt attgcgcgcg cgaacgcgat    300
tatcgccygg attattgggg ccagggcagc ctggtgaccg tgagcagcgg c             351
```

<210> SEQ ID NO 6
<211> LENGTH: 117
<212> TYPE: PRT
<213> ORGANISM: Artificial
<220> FEATURE:
<223> OTHER INFORMATION: Human Lysozyme -binding mutated VH

<400> SEQUENCE: 6

```
Gln Val Gln Leu Gln Glu Ser Gly Pro Gly Leu Val Arg Pro Ser Gln
1               5                   10                  15
```

Thr Leu Ser Leu Thr Cys Thr Val Ser Gly Phe Ser Leu Thr Gly Tyr
            20                  25                  30

Gly Val Asn Trp Phe Arg Gln Pro Gly Arg Glu Arg Glu Trp Ile
        35                  40                  45

Gly Met Ile Trp Gly Asp Gly Asn Thr Asp Tyr Asn Ser Ala Leu Lys
50                      55                  60

Ser Arg Val Thr Met Leu Lys Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Gly
            115

<210> SEQ ID NO 7
<211> LENGTH: 375
<212> TYPE: DNA
<213> ORGANISM: Artificial
<220> FEATURE:
<223> OTHER INFORMATION: Human Lysozyme -binding VHH coding DNA

<400> SEQUENCE: 7
ccatggcagg tgcagctgca ggaaagcggc ggtggcagcg tgcaggcggg cggtagcctg      60
cgcctgagct gcagcgcgag cggctatacc tatattagcg gctggtttcg ccaggcgccg     120
ggcaaagaac gcgaaggcgt ggcggcgatt cgcagcagcg atggcaccac ctattatgcg     180
gatagcgtga aaggccgctt taccattagc caggataatg cgaaaaatac cgtgtatctg     240
cagatgaata gcctgaaacc ggaagatacc gcgatgtatt attgcgcggc gaccgaagtg     300
gcgggctggc cgctggatat tggcatttat gattattggg gccagggcac cgaagtgacc     360
gtgagcagcg atatc                                                      375

<210> SEQ ID NO 8
<211> LENGTH: 125
<212> TYPE: PRT
<213> ORGANISM: Artificial
<220> FEATURE:
<223> OTHER INFORMATION: Human Lysozyme -binding VHH

<400> SEQUENCE: 8

Pro Trp Gln Val Gln Leu Gln Glu Ser Gly Gly Gly Ser Val Gln Ala
1               5                   10                  15

Gly Gly Ser Leu Arg Leu Ser Cys Ser Ala Ser Gly Tyr Thr Tyr Ile
            20                  25                  30

Ser Gly Trp Phe Arg Gln Ala Pro Gly Lys Arg Glu Gly Val Ala
        35                  40                  45

Ala Ile Arg Ser Ser Asp Gly Thr Thr Tyr Tyr Ala Asp Ser Val Lys
50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Ala
                85                  90                  95

Ala Thr Glu Val Ala Gly Trp Pro Leu Asp Ile Gly Ile Tyr Asp Tyr
            100                 105                 110

Trp Gly Gln Gly Thr Glu Val Thr Val Ser Ser Glu Phe
        115                 120                 125

<210> SEQ ID NO 9
<211> LENGTH: 363
<212> TYPE: DNA
<213> ORGANISM: Artificial
<220> FEATURE:
<223> OTHER INFORMATION: Human Lysozyme -binding mutated VH coding DNA

<400> SEQUENCE: 9

```
ccatggcagg tgcagctgca ggaaagcggc ccgggcctgg tgcgcccgag ccagaccctg      60
agcctgacct gcaccgtgag cggctttagc ctgaccggct atggcgtgaa ttggtttcgc     120
cagccgccgg gccgcgaacg cgaatggatt ggcatgattt ggggcgatgg caataccgat     180
tataatagcg cgctgaaaag ccgcgtgacc atgctgaaag ataccagcaa taatcagttt     240
agcctgcgcc tgagcagcgt gaccgcggcg gataccgcgg tgtattattg cgcgcgcgaa     300
cgcgattatc gccyggatta ttggggccag ggcagcctgg tgaccgtgag cagcggcgaa     360
ttc                                                                   363
```

<210> SEQ ID NO 10
<211> LENGTH: 121
<212> TYPE: PRT
<213> ORGANISM: Artificial
<220> FEATURE:
<223> OTHER INFORMATION: Human Lysozyme -binding mutated VH

<400> SEQUENCE: 10

```
Pro Trp Gln Val Gln Leu Gln Glu Ser Gly Pro Gly Leu Val Arg Pro
1               5                   10                  15

Ser Gln Thr Leu Ser Leu Thr Cys Thr Val Ser Gly Phe Ser Leu Thr
            20                  25                  30

Gly Tyr Gly Val Asn Trp Phe Arg Gln Pro Pro Gly Arg Glu Arg Glu
        35                  40                  45

Trp Ile Gly Met Ile Trp Gly Asp Gly Asn Thr Asp Tyr Asn Ser Ala
    50                  55                  60

Leu Lys Ser Arg Val Thr Met Leu Lys Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Glu Arg Asp Tyr Arg Leu Asp Tyr Trp Gly Gln Gly Ser
            100                 105                 110

Leu Val Thr Val Ser Ser Gly Glu Phe
        115                 120
```

<210> SEQ ID NO 11
<211> LENGTH: 184
<212> TYPE: DNA
<213> ORGANISM: Artificial
<220> FEATURE:
<223> OTHER INFORMATION: G3-jun coding DNA
<220> FEATURE:
<221> NAME/KEY: misc_feature
<222> LOCATION: (1)..(4)
<223> OTHER INFORMATION: n is a, c, g, or t

<400> SEQUENCE: 11

```
nnnngaatcc ggcgggggcg gtagcggcgg tggcgggtcg ggcggtggcg gatcgcgtat      60
cgctcgtctc gaggaaaaag ttaaaaccct gaaagctcag aactccgaac tggcttccac     120
cgctaacatg ctgcgtgaac aggttgctca gctgaaacag aaagttatga actacaggct     180
ttgc                                                                  184
```

<210> SEQ ID NO 12
<211> LENGTH: 60
<212> TYPE: PRT
<213> ORGANISM: Artificial
<220> FEATURE:
<223> OTHER INFORMATION: G3-Jun

<400> SEQUENCE: 12

Glu Phe Gly Gly Gly Gly Ser Gly Gly Gly Gly Ser Gly Gly Gly Gly
1               5                   10                  15

Ser Arg Ile Ala Arg Leu Glu Glu Lys Val Lys Thr Leu Lys Ala Gln
            20                  25                  30

Asn Ser Glu Leu Ala Ser Thr Ala Asn Met Leu Arg Glu Gln Val Ala
        35                  40                  45

Gln Leu Lys Gln Lys Val Met Asn Tyr Arg Leu Cys
    50                  55                  60

<210> SEQ ID NO 13
<211> LENGTH: 184
<212> TYPE: DNA
<213> ORGANISM: Artificial
<220> FEATURE:
<223> OTHER INFORMATION: G3-Fos coding DNA
<220> FEATURE:
<221> NAME/KEY: misc_feature
<222> LOCATION: (1)..(4)
<223> OTHER INFORMATION: n is a, c, g, or t

<400> SEQUENCE: 13
nnnngaatcc ggcggggggcg gtagcggcgg tggcgggtcg ggcggtggcg gatcgctgac      60
cgacaccctg caggctgaaa ccgaccagct ggaagacaaa aaatccgctc tgcagaccga     120
aatcgctaac ctgctgaaag aaaaagaaaa actggaattt atcctggctg cttacaggct     180
ttgc                                                                  184

<210> SEQ ID NO 14
<211> LENGTH: 60
<212> TYPE: PRT
<213> ORGANISM: Artificial
<220> FEATURE:
<223> OTHER INFORMATION: G3-Fos

<400> SEQUENCE: 14

Glu Phe Gly Gly Gly Gly Ser Gly Gly Gly Gly Ser Gly Gly Gly Gly
1               5                   10                  15

Ser Leu Thr Asp Thr Leu Gln Ala Glu Thr Asp Gln Leu Glu Asp Lys
            20                  25                  30

Lys Ser Ala Leu Gln Thr Glu Ile Ala Asn Leu Leu Lys Glu Lys Glu
        35                  40                  45

Lys Leu Glu Phe Ile Leu Ala Ala Tyr Arg Leu Cys
    50                  55                  60

<210> SEQ ID NO 15
<211> LENGTH: 531
<212> TYPE: DNA
<213> ORGANISM: Artificial
<220> FEATURE:
<223> OTHER INFORMATION: HuLA G3-Jun coding DNA

<400> SEQUENCE: 15
caggtgcagc tgcaggaaag cggcccgggc ctggtgcgcc cgagccagac cctgagcctg      60
acctgcaccg tgagcggctt tagcctgacc ggctatggct gaattggtt tcgccagccg     120 ccgggccgcg aacgcgaatg gattggcatg atttggggcg atggcaatac cgattataat     180

```
agcgcgctga aaagccgcgt gaccatgctg aaagatacca gcaataatca gtttagcctg    240
cgcctgagca gcgtgaccgc ggcggatacc gcggtgtatt attgcgcgcg cgaacgcgat    300
tatcgccygg attattgggg ccagggcagc ctggtgaccg tgagcagcgg cgaatccggc    360
gggggcggta gcggcggtgg cgggtcgggc ggtggcggat cgcgtatcgc tcgtctcgag    420
gaaaaagtta aaccctgaa agctcagaac tccgaactgg cttccaccgc taacatgctg    480
cgtgaacagg ttgctcagct gaaacagaaa gttatgaact acaggctttg c    531
```

<210> SEQ ID NO 16
<211> LENGTH: 177
<212> TYPE: PRT
<213> ORGANISM: Artificial
<220> FEATURE:
<223> OTHER INFORMATION: HuL binding VHH-Jun
<220> FEATURE:
<221> NAME/KEY: misc_feature
<222> LOCATION: (103)..(103)
<223> OTHER INFORMATION: Xaa can be any naturally occurring amino acid

<400> SEQUENCE: 16

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Ser Leu Thr Gly Tyr
            20                  25                  30

Gly Val Asn Trp Phe Arg Gln Pro Pro Gly Arg Glu Arg Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Lys Asp Thr Ser Asn Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Xaa Asp Tyr Trp Gly Gln Gly Ser Leu Val
            100                 105                 110

Thr Val Ser Ser Gly Glu Ser Gly Gly Gly Ser Gly Gly Gly
        115                 120                 125

Ser Gly Gly Gly Gly Ser Arg Ile Ala Arg Leu Glu Glu Lys Val Lys
130                 135                 140

Thr Leu Lys Ala Gln Asn Ser Glu Leu Ala Ser Thr Ala Asn Met Leu
145                 150                 155                 160

Arg Glu Gln Val Ala Gln Leu Lys Gln Lys Val Met Asn Tyr Arg Leu
                165                 170                 175

Cys

<210> SEQ ID NO 17
<211> LENGTH: 531
<212> TYPE: DNA
<213> ORGANISM: Artificial
<220> FEATURE:
<223> OTHER INFORMATION: HuLB G3 Fos coding DNA

<400> SEQUENCE: 17

```
caggtgcagc tgcaggaaag cggcccgggc ctggtgcgcc cgagccagac cctgagcctg    60
acctgcaccg tgagcggctt tagcctgacc ggctatggcg tgaattggtt tcgccagccg    120
ccgggccgcg aacgcgaatg gattggcatg atttggggcg atggcaatac cgattataat    180
agcgcgctga aaagccgcgt gaccatgctg aaagatacca gcaataatca gtttagcctg    240
```

```
cgcctgagca gcgtgaccgc ggcggatacc gcggtgtatt attgcgcgcg cgaacgcgat    300
tatcgccygg attattgggg ccagggcagc ctggtgaccg tgagcagcgg cgaatccggc    360
gggggcggta gcggcggtgg cgggtcgggc ggtggcggat cgctgaccga caccctgcag    420
gctgaaaccg accagctgga agacaaaaaa tccgctctgc agaccgaaat cgctaacctg    480
ctgaaagaaa aagaaaaact ggaatttatc ctggctgctt acaggctttg c             531

<210> SEQ ID NO 18
<211> LENGTH: 177
<212> TYPE: PRT
<213> ORGANISM: Artificial
<220> FEATURE:
<223> OTHER INFORMATION: HuLB G3 Fos
<220> FEATURE:
<221> NAME/KEY: misc_feature
<222> LOCATION: (103)..(103)
<223> OTHER INFORMATION: Xaa can be any naturally occurring amino acid

<400> SEQUENCE: 18

Gln Val Gln Leu Gln Glu Ser Gly Pro Gly Leu Val Arg Pro Ser Gln
 1               5                  10                  15

Thr Leu Ser Leu Thr Cys Thr Val Ser Gly Phe Ser Leu Thr Gly Tyr
            20                  25                  30

Gly Val Asn Trp Phe Arg Gln Pro Pro Gly Arg Glu Arg Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Lys Asp Thr Ser Asn Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Xaa Asp Tyr Trp Gly Gln Gly Ser Leu Val
            100                 105                 110

Thr Val Ser Ser Gly Glu Ser Gly Gly Gly Ser Gly Gly Gly Gly
        115                 120                 125

Ser Gly Gly Gly Gly Ser Leu Thr Asp Thr Leu Gln Ala Glu Thr Asp
    130                 135                 140

Gln Leu Glu Asp Lys Lys Ser Ala Leu Gln Thr Glu Ile Ala Asn Leu
145                 150                 155                 160

Leu Lys Glu Lys Glu Lys Leu Glu Phe Ile Leu Ala Ala Tyr Arg Leu
                165                 170                 175

Cys
```